(12) United States Patent
Michelotti

(10) Patent No.: US 6,613,517 B2
(45) Date of Patent: Sep. 2, 2003

(54) NUCLEIC ACID BINDING ASSAY AND SELECTION METHOD

(75) Inventor: Emil F. Michelotti, Foster City, CA (US)

(73) Assignee: Genelabs Technologies, Inc., Redwood City, CA (US)

( * ) Notice: Subject to any disclaimer, the term of this patent is extended or adjusted under 35 U.S.C. 154(b) by 0 days.

(21) Appl. No.: 09/764,043

(22) Filed: Jan. 16, 2001

(65) Prior Publication Data

US 2002/0055104 A1 May 9, 2002

Related U.S. Application Data

(60) Provisional application No. 60/176,249, filed on Jan. 15, 2000.

(51) Int. Cl.[7] ............................. C12Q 1/68; G01N 33/53
(52) U.S. Cl. .............................................. 435/6; 435/7.1
(58) Field of Search ............................ 435/6, 91.2, 7.1

(56) References Cited

U.S. PATENT DOCUMENTS 5,124,246 A  *  6/1992  Urdea et al. .................... 435/6
5,738,990 A     4/1998  Edwards et al.
5,912,145 A  *  6/1999  Stanley ...................... 435/91.1

FOREIGN PATENT DOCUMENTS

WO    WO 99/63117    12/1999

OTHER PUBLICATIONS

Boger, D.L. et al. (2000) "Total Synthesis of Distamycin A and 2640 Analogues: A Solution–Phase Combinatorial Approach to the Discovery of New, Bioactive DNA Binding Agents and Development of a Rapid, High–Throughput Screen for Determining Relative DNA Binding Affinity or DNA Binding Sequence Selectivity," *J. Am. Chem. Soc.* 122:6382–6394.

Dervan, P.B. et al. "Sequence–specific DNA recognition by plyamides" *Biopolymers*, 688–693.

Devchand, P.R. et al. (1993) "Uracil–DNA glycosylase as a probe for protein—DNA interactions" *Nucleic Acids Research*, vol. 21, No. 15; 3437–3443.

Geierstanger, B.H. et al. (1994) "Design of a G–C–Specific DNA Minor Groove–Binding Peptide" *Science* vol. 266:646–650.

Hardenbol, P. et al. (1997) "Identification of preferred hTBP DNA binding sites by the combinatorial method REPSA" *Nucleic Acids Research* vol. 25, No. 16, 3339–3344.

Parikh, S.S. et al. (1998) "Base excision repair initiation revealed by crystal structures and binding kinetics of human uracil–DNA glycosylase with DNA" *The EMBO Journal* vol. 17 No. 17. pp. 5214–5226.

Slupphaug, G. et al. (1996) "A nucleotide–flipping mechanism from the structure of human uracil–DNA glycosylase bound to DNA" *Nature*, vol. 384: 87–92.

Guille, Matthew, J. et al. (1997) "Methods for the Analysis of DNA–Protein Interactions" *Molecular Biotechnology* vol. 8 pp. 35–52.

Thiesen et al. (1990) "Target Detection Assay (TDA): a versatile procedure to determine DNA binding sites as demonstrated on SP1 protein" *Nucleic Acids Research* vol. 18, No. 11, pp. 3203–3209.

Klug, et al., (1994) "All you wanted to know about SELEX" *Molecular Biology Reports* vol. 20: 97–107.

Speck et al, "From footprint to toeprint: a close up of the DNA–A box, the binding site for the bacterial initiator protein DNA–A", Nucleic Acids Research (1997) 25(16):3242–3247.*

Pu et al, "Uracil interference, a rapid and general method for defining protein–DNA interactions involving the 5–methyl group of thymines: the GCN–4–DNA complex", Nucleic Acids Research (1992) 20(4):771–775.*

Stratagene Catalog (1988) p. 39.*

* cited by examiner

*Primary Examiner*—Eggerton A. Campbell

(57) ABSTRACT

The invention provides a novel nucleic acid binding assay, which is useful for assessing the sequence-dependence of the binding of ligands to nucleic acid molecules, as well as for determining the affinity of the binding interaction. The invention also provides a selection method based on this nucleic acid binding assay. This selection method allows co-selection of ligands and the nucleic acid molecules that they bind. Additionally, the invention provides kits that can be used for carrying out the methods of the invention.

47 Claims, 4 Drawing Sheets

MINOR GROOVE BINDING PROTEIN LIBRARY

Round 2 of selection

Amplified phage which bound
column in first round

Column with amplified oligos
which were protected from
UDG in first round

NUCLEIC ACID BINDING ASSAY AND SELECTION METHOD

CROSS-REFERENCE TO RELATED APPLICATIONS

This application claims priority to and benefit of U.S. Ser. No. 60/176,249, filed on Jan. 15, 2000; as provided for under 35 U.S.C. §119 and/or 35 U.S.C. §120, as appropriate. U.S. Ser. No. 60/176,249 is incorporated herein by reference, in its entirety, for all purposes.

FIELD OF THE INVENTION

The present invention relates to an assay and kit for screening a ligand for its ability to bind to one or more nucleotide sequences in a nucleic acid target. The invention also relates to a selection method employing this assay and a kit for performing the selection method.

BACKGROUND OF THE INVENTION

In order to discover new compounds capable of controlling the expression of levels of a selected protein, it is necessary to (i) identify one or more unique promoter-region sequences that can serve as a target for regulation of gene expression under the control of that promoter, and (ii) identify compounds capable of binding to such unique promoter sequences. It would be desirable, therefore, to provide a simple, reliable assay for screening compounds for their ability to bind to particular nucleic acid sequences, especially duplex base sequences (e.g., specific sequences or sequences rich in particular bases) in double-stranded DNA, and to provide kits including nucleic acid reagents for carrying out such assays.

SUMMARY OF THE INVENTION

The invention provides a nucleic acid binding assay for screening a ligand for its ability to bind to a nucleotide sequence in a nucleic acid molecule. The binding assay employs a nucleic acid molecule having a first region and second region, adjacent to the first region. The first region includes a first site that is susceptible to modification by a modifying agent, wherein the modification is effective to block strand-directed duplication by a polymerase enzyme at the first site. The binding assay entails contacting the nucleic acid molecule with a ligand, under conditions suitable for sequence-dependent binding of the ligand to the nucleic acid molecule. The resultant reaction mixture is treated with the modifying agent, under conditions such that nucleic acid molecules having a ligand bound to the second region are substantially protected from modification at the first site, and nucleic acid molecules that do not have a ligand bound to the second region are substantially modified at the first site. After treatment with the modifying agent, the nucleic acid molecule is contacted with the polymerase enzyme, under conditions wherein only unmodified nucleic acid strands are amplified, and this amplification therefore indicates that the ligand binds to a nucleotide sequence in the second region. If desired, the amplification product can be subjected to an additional round of ligand binding, modification, and amplification.

In preferred embodiments, the nucleic acid molecule is a double-stranded nucleic acid molecule, the first and second regions are first and second duplex regions, the first site is on a first strand of the nucleic acid molecule, and only the first strand is amplified.

In one embodiment, the first site includes a non-standard nucleotide that is modified by the modifying agent, and the modification is effective to block strand-directed duplication by the polymerase enzyme at the first site. In this embodiment, where the nucleic acid molecule is a DNA molecule, the modifying agent can be a prokaryotic or eukaryotic repair enzyme that recognizes and removes the non-standard nucleotide from duplex DNA or DNA/RNA duplexes.

In a variation of this embodiment, the nucleic acid molecule includes a second strand including one or more non-standard nucleotides that can be modified by a modifying agent. The modifying agent can be the same as or different from that used to modify the first site. Treatment with this modifying agent is effective to modify the non-standard nucleotide(s) in the second strand, which blocks strand-directed duplication of the second strand by the polymerase enzyme.

In an alternative embodiment, the modifying agent is a restriction enzyme and the first site includes a recognition site for the restriction enzyme.

The modifying agent(s) is/are preferably removed or inactivated prior to amplification of unmodified nucleic acid strands, which is preferably carried out by primer-directed PCR amplification.

In one embodiment, a set of different nucleic acid molecules that include different nucleotide sequences in the second region is assayed. In this embodiment, the method preferably includes determining the nucleotide sequence of the amplification product in the second region to determine whether the ligand shows binding specificity for one or more nucleotide sequences in the second region. This embodiment can be used for high-throughput screening of ligands and nucleic acid molecules.

The nucleic acid binding assay of the invention can be used to assess the binding affinity of the ligand-nucleic acid molecule interaction. In this case, the method additionally includes determining the concentration of the ligand that protects approximately 50 percent of the first sites from modification as an indication of the dissociation constant ($K_d$) of the ligand. Where the amplification of unmodified nucleic acids is carried out by primer-directed PCR amplification, approximately 50 percent protection can determined by determining the concentration of ligand that gives a Ct value about 2 higher than the Ct value obtained when the nucleic acid molecule amplified without prior exposure to ligand or modifying enzyme.

The invention also provides a nucleic acid selection method that is based on the nucleic acid binding assay of the invention. The selection method can be used to screen a set of ligands for the ability to bind to nucleotide sequence(s) in a set of nucleic acid molecules, allowing, in effect, co-selection of ligands and their cognate binding sites. Each member of the set of nucleic acid molecules has a first region and a second region, adjacent to the first region. In the first region, the nucleic acid molecules include a first site that is susceptible to modification by a modifying agent, and such modification is effective to block strand-directed duplication by a polymerase enzyme at the first site. The nucleic acid molecules include different nucleotide sequences in the second region.

The selection method entails contacting the nucleic acid molecule with a ligand, under conditions suitable for sequence-dependent binding of one or more ligands to one or more nucleic acid molecules. The resultant reaction mixture is treated with the modifying agent, under conditions such that nucleic acid molecules having a ligand bound to the second region are substantially protected from modification at the first site, and nucleic acid molecules that do not have a ligand bound to the second region are substantially modified at the first site. After this treatment, the modifying agent is typically removed or inactivated before continuing on with the method.

Ligands that bind to the nucleic acid molecules are then separated from unbound ligands, and the ligands that bind to the nucleic acid molecules are recovered. In one embodiment, bound/unbound separation is facilitated by employing nucleic acid molecules linked to a substrate; unbound ligands are removed from the substrate by washing, and then bound ligands are eluted off of the substrate. Also, after treatment with the modifying agent, the set of nucleic acid molecules is contacted with the polymerase enzyme, under conditions wherein only unmodified nucleic acid strands are amplified. The selection method thus produces a pool of selected ligands that bind in a sequence-dependent manner to one or more nucleotide sequences present in a pool of selected nucleic acid molecules.

In preferred embodiments of the selection method, the ligands are heterologous peptides, expressed on the surface of phage particles, each phage particle includes a nucleic acid molecule encoding the heterologous peptide expressed on its surface, and thus the pool of selected ligands is a pool of selected phage particles. In one such embodiment, the method includes an additional round of selection that entails amplifying the pool of selected phage particles to produce amplified, selected phage particles, and contacting the pool of selected nucleic acid molecules with the amplified, selected phage particles, under conditions suitable for specific binding of one or more heterologous peptides to one or more nucleic acid molecules. The resultant reaction mixture is treated with the modifying agent, under conditions wherein nucleic acid molecules having a heterologous peptide bound to the second region are substantially protected from modification, and nucleic acid molecules that do not have a heterologous peptide bound to the second region are substantially modified at the first site. The modifying agent is then removed or inactivated.

The amplified, selected phage particles that bind to the selected nucleic acid molecules are then separated from unbound amplified, selected phage particles, and the amplified, selected phage particles that bind to the selected nucleic acid molecules are recovered. Also, after treatment with the modifying agent, the selected nucleic acid molecules are contacted with the polymerase enzyme, under conditions wherein only unmodified nucleic acid molecules are amplified. One additional round of selection thus produces a pool of twice-selected phage particles that bind in a sequence-dependent manner to one or more nucleotide sequences present in a pool of twice-selected nucleic acid molecules. Further rounds of selection can be carried out, if desired.

When the selection method employs substrate-linked nucleic acid molecules, the nucleic acid molecules can be reversibly linked to a substrate, and the selection method can include releasing the nucleic acid molecules from the substrate before amplification of the first strands.

The invention also includes a kit for use in screening one or more ligands for the ability to bind to nucleotide sequence(s) in nucleic acid molecules. The kit includes a set of nucleic acid molecules, each having a first region and a second region, adjacent to the first region. The first region includes a first site that is susceptible to modification by a modifying agent, and such modification is effective to block strand-directed duplication by a polymerase enzyme at the first site. The nucleic acid molecules include different nucleotide sequences in the second region. The kit also includes the modifying agent.

In preferred embodiments, the nucleic acid molecules in the set are double-stranded nucleic acid molecules, the first and second regions are first and second duplex regions, and the first site is on a first strand of the nucleic acid molecules.

In one embodiment, the first site includes a non-standard nucleotide that is modified by the modifying agent, and the modification is effective to block strand-directed duplication by the polymerase enzyme at the first site. In this embodiment, where the nucleic acid molecules are DNA molecules, the modifying agent can be a prokaryotic or eukaryotic repair enzyme that recognizes and removes the non-standard nucleotide from duplex DNA. In a variation of this embodiment, the nucleic acid molecules each include a second strand including one or more non-standard nucleotides that can be modified by the modifying agent.

In an alternative embodiment, the modifying agent is a restriction enzyme and the first site includes a recognition site for the restriction enzyme.

In a preferred embodiment, the kit includes primers that specifically bind sites flanking the first and second regions of the nucleic acid molecules and are useful for amplifying the first and second regions of the nucleic acid molecules.

If the kit is intended for use in the selection method of the invention, the nucleic acid molecules are preferably linked to a substrate. In one embodiment, this linkage is a reversible linkage. The kit can also include a phage display library, which can be screened to identify those phage displaying heterologous peptides that bind to one or more nucleotide sequences in the set of nucleic acid molecules.

DETAILED DESCRIPTION

Definitions

Figure 1:
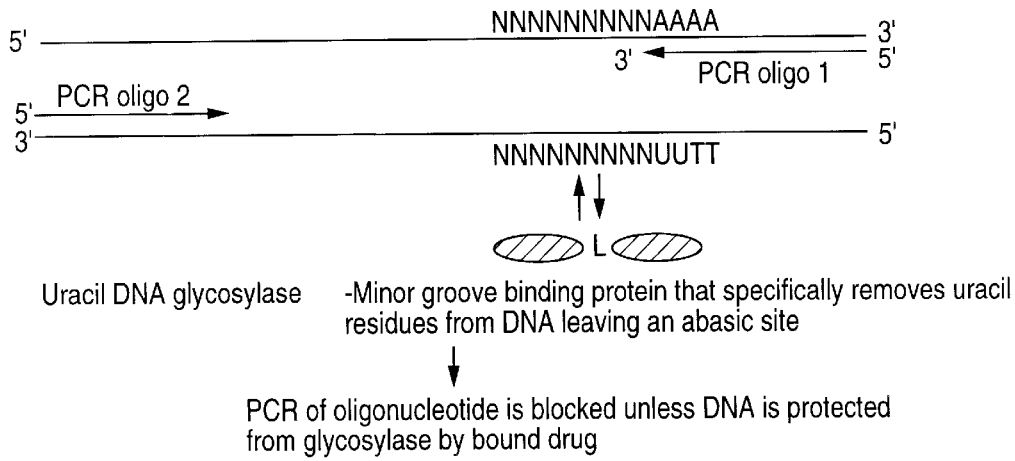
FIG. 1 is a schematic diagram showing a preferred embodiment of the general ligand-nucleic acid binding assay described herein.
Figure 2:
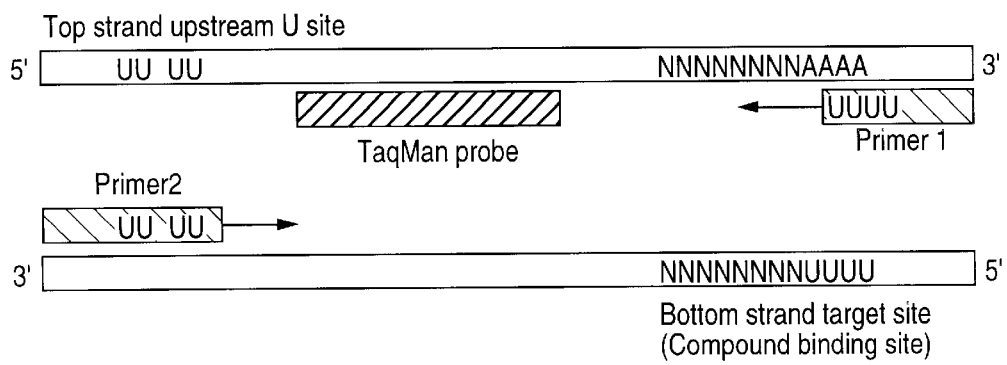
FIG. 2 illustrates a preferred variation of the embodiment shown in FIG. 1, wherein a duplex oligonucleotide is depicted by open boxes and N depicts a sequence position that may be occupied by any nucleic acid residue. The two dotted boxes represent PCR primers, and the arrows represent the direction of the polymerase reaction. The "top strand upstream U site" prevents the top strand from being amplified and the "bottom strand target site" is the ligand binding site. The hatched box marks the position of the TaqMan™ probe, and all residues are G or C except where indicated.
Figure 3A:
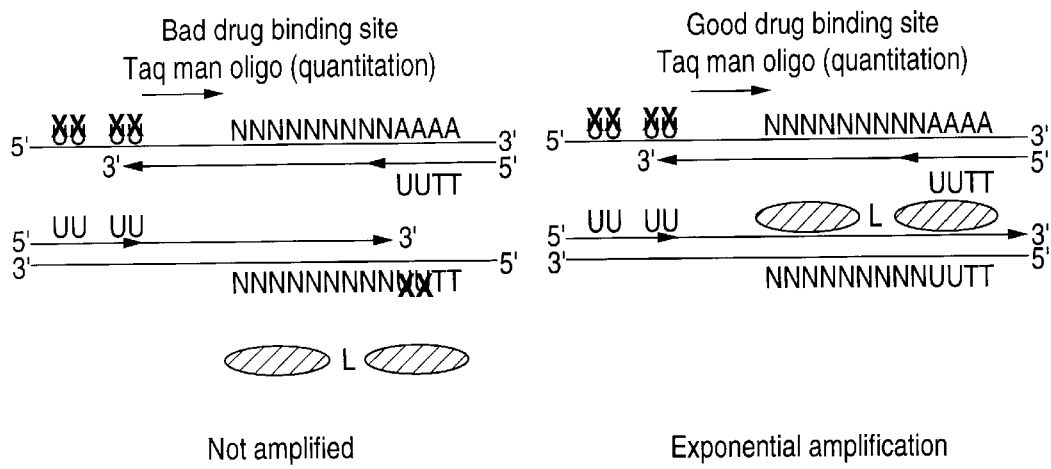
FIG. 3A illustrates an exemplary embodiment of the ligand-nucleic acid binding assay wherein two different test duplex oligonucleotides have a lower strand containing either good ligand binding site or a bad ligand binding site.
Figure 3B:
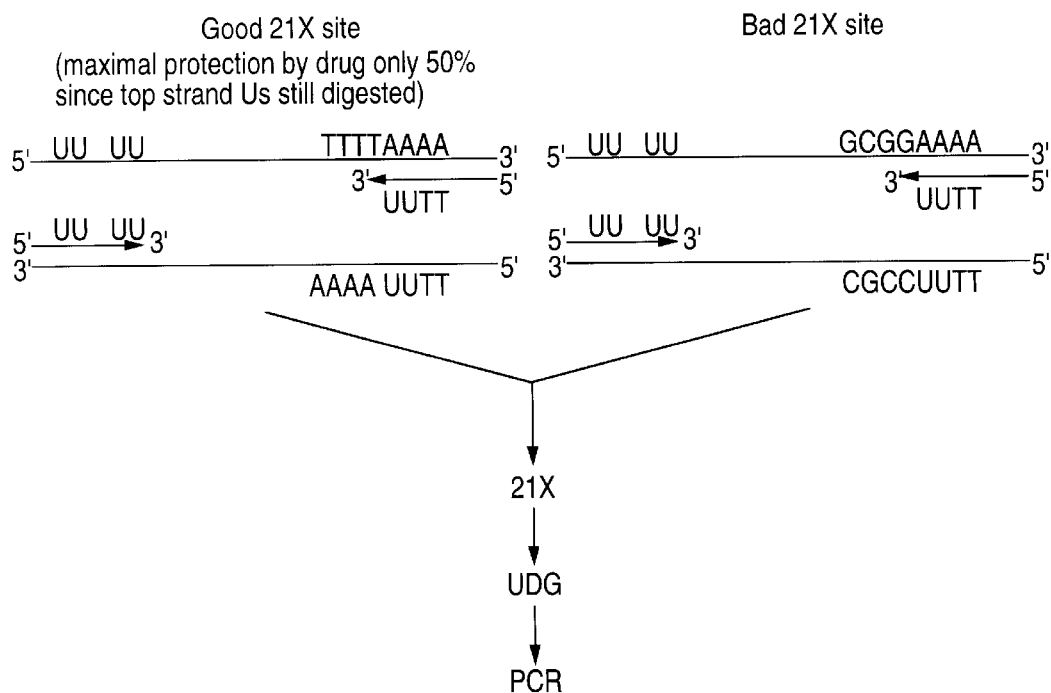
FIG. 3B illustrates a specific example of the embodiment of FIG. 3A, wherein the two different test duplex oligonucleotides have a lower strand containing either an AT-rich ("good") sequence or a GC-rich rich ("bad") binding sequence for the DNA binding compound, 21X.

Unless otherwise indicated, all terms used herein have the same meaning as they would to one skilled in the art of the present invention. Practitioners are particularly directed to Sambrook et al. (1989) Molecular Cloning: A Laboratory Manual (Second Edition), Cold Spring Harbor Press, Plainview, N.Y. and Ausubel FM et al. (1989) Current Protocols in Molecular Biology, John Wiley & Sons, New York, N.Y., for definitions and terms of the art. It is to be understood that this invention is not limited by the particular methodology, protocols, and reagents described, as these may vary.

The term "nucleic acid molecule" refers to a deoxyribonucleotide or ribonucleotide polymer, and unless otherwise limited, includes known analogs of natural nucleotides that can function in a similar manner to naturally occurring nucleotides. The terms "polynucleotide" and "oligonucleotide" are used interchangeably with the term "nucleic acid molecule."

The term "nucleic acid molecule" refers any form of DNA or RNA, including, for example, genomic DNA; complementary DNA (cDNA), which is a DNA representation of MRNA, usually obtained by reverse transcription of messenger RNA (mRNA) or amplification; DNA molecules produced synthetically or by amplification; and mRNA.

The term "nucleic acid molecule" encompasses double-stranded nucleic acid molecules, as well as single-stranded molecules. The strands of double-stranded nucleic acid molecules are said to be "complementary" and are referred to as the "complements" of one another.

As used herein, the term "complementary" refers to the capacity for precise pairing between two nucleotides; i.e., if a nucleotide at a given position of a nucleic acid molecule is capable of hydrogen bonding with a nucleotide of another nucleic acid molecule, then the two nucleic acid molecules are considered to be complementary to one another at that position. In the case of standard Watson-Crick basepairing, an A on one strand pairs with a T on the opposite strand, and an G on one strand pairs with a C on the opposite strand. Thus, the depiction of a single strand defines the sequence of the other strand and thus also includes the complement of the sequence.

Nucleic acid subunits are referred to herein by their standard base designations: T, thymine; A, adenosine; C, cytosine; G, guanine, U, uracil; variable positions are referred to as described below.

As used herein, the term "natural nucleotide" refers to residues A, C, G, and T for DNA and A, C, G, and U for RNA.

Accordingly, as used herein, the term "non-standard nucleotide" refers to nucleotides other than a "natural nucleotide." For example, a deoxyuracil or dU present in a DNA sequence would be considered a non-standard nucleotide, since the normal A-binding nucleotide in duplex DNA is dT. Other non-standard nucleotides include those having modified bases, such as 8-oxoguanine; formamidopyridine residues, such as 2,6-diamino-4-hydroxyl-5-methylformamidopyrimidine; and thymine glycol. In particular, non-standard nucleotides that are cleaved or whose bases are removed by a prokaryotic or eukaryotic endonuclease repair enzyme, including non-standard pyrimidine nucleotides are suitable for use in the invention.

The terms "nucleotide sequence" and "oligomeric sequence" are used interchangeably herein to refer to a sequence of nucleotide residues in a nucleic acid molecule.

Nucleic acid molecules of the invention include adjacent first and second regions and can be used in screening candidate compounds for DNA-binding properties. As used herein, the term "first region" refers to a segment of a single- or double-stranded nucleic acid molecule. The first region preferably includes at least about 1 to about 6 nucleotides (per strand), more preferably at least about 2 to about 4 nucleotides (per strand), and most preferably about 2 nucleotides (per strand). The first region includes a first site that is susceptible to modification by a nucleic acid modifying agent, e.g., at least one non-standard nucleotide. The first region in a double-stranded nucleic acid molecule is also referred to herein as a "first duplex region."

The term "site" encompasses a single nucleotides, as well as sequence of nucleotides, within a nucleic acid molecule.

As used herein, the term "second region" refers to a segment of a single- or double-stranded nucleic acid molecule, wherein the segment typically has at least about 3 to about 11, and preferably at least about 4 to about 9 nucleotides. In preferred embodiments employed a set of nucleic acid molecules, the second region includes a variable sequence component, i.e., wherein the nucleotide sequences differs for different nucleic acid molecules in the set. For example, the set can include any of the four natural nucleotides at one or more given position in the second region. The variable sequence components of the second region can influence the specificity and affinity of binding of candidate ligands. The second region in a double-stranded nucleic acid molecule is also referred to herein as a "second duplex region."

As used with reference to the first and second regions, the term "adjacent" means that the regions are sufficiently close that a modifying agent according to the invention interacts with both regions.

The term "ligand" refers to any molecule that is capable of specifically binding to another molecule. The invention concerns ligands that are characterized by sequence-dependent binding to nucleic acid molecules. Such ligands include macromolecules, such as peptides or polypeptides, as well as small molecules. Generally, "small molecules" have molecular weights of less than about 10,000 Daltons, preferably less than about 2,000 Daltons, and more preferably less than about 1,000 Daltons. Accordingly, the terms "ligand" and "compound" are used interchangeably herein. Preferred ligands or compounds bind preferentially or specifically at a sequence that is adjacent (i.e., flanking), overlapping, or the same as, the DNA binding site for a transcriptional regulatory protein.

As used herein, the term "sequence-dependent binding" refers to the binding of molecules to DNA in a manner that is dependent upon the target nucleotide sequence. That is, a sequence-dependent binder binds to a particular type of sequence in preference to different types of sequences. Such binding may be "sequence-preferential," for example, exhibiting a preference for an AT-rich or GC-rich sequence, or "sequence-specific," that is, binding to a specific sequence or group of related sequences with a higher binding affinity than to other sequences.

An "AT-rich sequence" is a nucleotide sequence in which at least 50% of the nucleotides in the sequence are A or T. Similarly, a "GC-rich sequence" is a nucleotide sequence in which at least 50% of the nucleotides are G or C.

As used herein, the term "dimer" refers to a composition that has two subunits that are covalently or non-covalently linked to one another and that may or may not have the same chemical structure. A "multimer" is a composition having more than two such subunits.

Binding affinity is expressed herein in terms of the dissociation constant ($K_d$), which represents the concentration of a ligand required to occupy 50% of binding sites in a binding reaction.

As applied to nucleic acid molecules, the terms "amplify," "amplified," "amplification," etc., are used herein refer to an exponential amplification reaction in which each nucleic acid strand produced in the reaction is capable of serving as a template for the synthesis of an addition strand, i.e., includes a primer site to which a primer in the reaction mixture can bind. According, the phrase "only unmodified nucleic acid strands are amplified" indicates that only unmodified nucleic acid strands undergo exponential amplification during the amplification reaction. Modified nucleic acid strands in the reaction mixture, which may or may not undergo linear amplification, are said to be "incapable of amplification" because they do not undergo exponential amplification. An amplification product produced as described herein may, however, include the products of linear and exponential amplification. But the products of exponential amplification are generally present in much higher amounts than the products of linear amplification.

As used herein, the "threshold cycle" (Ct) value is the polymerase chain reaction (PCR) amplification cycle at which a fluorescent signal, e.g., from a fluorescent oligonucleotide probe used in real-time fluorescence-based quantitation of PCR (such as the TaqMan™ probe) is first detectable above background.

A "phage display library" refers to a collection of phage (e.g., filamentous phage) wherein the phage express an external (typically heterologous) protein. The external protein is free to interact with (bind to) other moieties with which the phage are contacted.

I. Nucleic Acid Binding Assay

In General

The nucleic acid binding assay of the invention is directed to screening candidate compounds for the ability to bind to one or more selected oligomeric sequences. The binding assay can be used, for example, to determine the preferred or optimal nucleotide sequence of a binding site for candidate compounds to nucleic acid molecules and, optionally, to determine the binding affinity of a candidate compound for a particular nucleotide sequence. The assay is based on the selective amplification of nucleic acid molecules that are bound by the candidate compound(s). Compound binding protects the nucleic acid molecules from subsequent modification upon treatment with a modifying agent. Nucleotide sequences that do not have high affinity for the candidate compound, that is, do not stably bind the candidate compound, are modified and thereby rendered incapable of strand amplification. After strand amplification, e.g., by PCR, the preferred or optimal sequences for the binding site can be determined by sequencing the selectively amplified strands.

Nucleic Acid Molecules

A schematic representation of the nucleic acid binding assay is presented in FIG. 1. Any type of nucleic acid molecule can be employed in the assay, but DNA is preferred. Nucleic acid molecules useful in the assay can be single-stranded or double-stranded, depending on the binding characteristics of the candidate compound. Double-stranded DNA molecules, typically, relatively short (e.g., less than about 100 nucleotides) synthetic oligonucleotides, are preferred for assaying the binding characteristics of compounds intended to substitute for, or inhibit, transcription factor binding.

Nucleic acid molecules employed in the assay have a first region and a second region, adjacent to the first region. A double-stranded nucleic acid according to the invention has a first (or lower, see FIG. 1) strand comprising a first region, preferably about 2 to about 6 residues, more preferably about 2 to about 4 residues, and most preferably about 2 residues, in length, and containing a site that is susceptible to modification by a modifying agent, such that if modified, strand-directed duplication by a polymerase enzyme is blocked.

Adjacent this first region in the first strand is a second region, typically about 3 about 11, and preferably about 4 to about 9, residues in length.

The nucleic acid binding assay determines the effect of nucleotide sequence in the second region upon binding of the candidate compound. More specifically, nucleic acid molecules useful in the assay are designed to test the ability of the candidate compound to bind in the second region and thereby prevent a modifying agent from modifying a site in the first region. Although typical sizes for the regions are given above, those of skill in the art appreciate that these regions are defined operationally and will vary depending on the type of modifying agent and candidate compound(s) employed in the assay.

In a preferred embodiment, a set of different nucleic acid molecules is assayed to determine preferred or optimal binding sequences. In this case, the first region contains, in addition to a site that is susceptible to modification, any nucleotides required for recognition and binding of the modifying agent to the nucleic acid molecule. Such nucleotides should be appropriately located to allow modification of the nucleic acid molecule at the susceptible site. Nucleotides required for recognition and binding of the modifying agent are preferably invariant between the different nucleic acid molecules. The second region contains a variable stretch of nucleotides located such that this stretch of nucleotides influences binding of the candidate compound to the nucleic acid molecule, which in turn, reduces the ability of the modifying agent to interact with and modify the susceptible site. In a preferred embodiment, the set of different nucleic acid molecules includes any of the four possible natural nucleotides at each variant position within the second region, i.e., fully degenerate sequences, allowing the assay of compound binding to all possible sequence combinations.

If information regarding the binding preferences of the candidate compound is available, nucleic acid molecules for use in the assay are generally designed such that the sequence composition of portions of the nucleic acid molecule other than the first and second regions do not contain preferred binding sequences for the candidate compound. For example, if the candidate compound shows a preference for AT-rich sequences, nucleic acid molecules for use in the assay are designed to have a greater GC content, to reduce binding outside of the first and second regions.

The make-up of the site in the first region that is susceptible to modification by a modifying agent varies depending on the agent selected. In a preferred embodiment, the modifying agent is an enzyme. Particularly preferred is a prokaryotic or eukaryotic repair enzyme that recognizes and removes a non-standard base from duplex DNA or DNA/RNA duplexes. Preferred enzymes include those that cleave the non-standard nucleotide at its backbone linkage or excise the nucleotide base. In this case, the nucleic acid includes, in the first region, a non-standard nucleotide that is recognized as a substrate by the enzyme employed in the assay. In various specific exemplary embodiments, the non-standard nucleotide(s) are uracil nucleotide(s) and the modifying agent is uracil DNA glycosylase; the non-standard nucleotide(s) are formamidopyrimidine or 8-oxoguanine nucleotide(s) and the modifying agent is formamidopyrimidine glycosylase; and the non-standard nucleotide(s) are thymine glycol nucleotide(s) and the modifying agent is *E. coli* endonuclease III.

In an alternative preferred embodiment, the susceptible site is either a binding site or a cleavage site for a restriction enzyme. For example, type I, II, and III restriction enzymes bind to specific sequences, which could be included in the susceptible site to screen for compounds that can bind to these specific sequences and prevent restriction enzyme binding and subsequent cleavage. Type IIS restriction enzymes cleave nucleic acid molecules at a precise distance from their binding sites. These enzymes could be used in the assay as described for the other restriction enzymes or, alternatively, the nucleic acid molecules can be designed so that the susceptible site includes the cleavage site, rather than the enzyme binding site. This embodiment offers the advantage that the sequence of the cleavage site is not restricted, which facilitates screening for compounds that bind to and protect any sequence of interest.

In preferred embodiments, the second (or upper, see FIG. 1) strand of the nucleic acid molecule also contains one or more non-standard nucleotides that can be modified by a modifying agent to prevent the second or upper strand from being amplified in the assay. More specifically, one or more non-standard nucleotides are preferably incorporated in a region distinct from the first and second regions discussed above, which are targeted by the candidate compound. The non-standard nucleotide(s) on the second strand are not protected from modification by candidate compound binding and are therefore modified upon exposure to the agent. Such modification is effective to block strand-directed duplication of the second strand during amplification. In a preferred embodiment, the non-standard nucleotide(s) is/are located 5' (i.e., upstream) of the first and second regions and either 3' (i.e., downstream) of an amplification primer site on the second strand or in the amplification primer site itself. In this embodiment, modification of the non-standard nucleotide(s) destroys the amplification primer site, thereby blocking amplification of this strand.

The modifying agent can be the same or different from that employed to modify the susceptible site on the first strand. For greater convenience, it is generally preferable to use one modifying agent for both reactions. Accordingly, preferred embodiments employ a non-standard nucleotide at the susceptible site on the first strand and the same non-standard nucleotide(s) in the upstream region on the second strand. Thus, the assay can be designed such that removal of a non-standard nucleotide from the upstream region prevents amplification of the second strand, regardless of candidate compound binding. In contrast, non-standard nucleotide removal from the susceptible site on the first strand depends on the binding of candidate compound to the second region of the nucleic acid molecule. That is, binding prevents or reduces modification of the susceptible site, allowing amplification of the first strands, and, lack of (or weak) binding results in modification of the susceptible site, in which case there is little (i.e., no more than background levels) or no amplification from either strand.

The nucleic acid molecules described herein can be prepared by any available method, most conveniently, standard solid-phase synthesis techniques, including techniques for introducing each of 4 different bases at each synthesis position to produce a mixture of degenerate sequences.

Ligands

The methods of the invention can be carried out with any ligand (see, e.g., the discussion of peptide ligands below in connection with the selection method of the invention). Thus, candidate compounds for use in the nucleic acid binding assay described herein can be polypeptides, peptides, oligonucleotides, and derivatives thereof, as well as small molecules, including biological or synthetic organic compounds (e.g., linear and cyclized polypyrroles, polyamides, and polyimidazoles) or even inorganic compounds. For example, the assay can be used to probe the binding requirements of transcriptional regulatory proteins (e.g., LEF-1), or derivatives thereof, with respect to their DNA response element sequences.

Small molecules are of particular interest because they are desirable as therapeutics for several reasons related to compound delivery: (i) they are commonly less than 10 kilodaltons molecular weight; (ii) they are likely to be permeable to cells; (iii) they may be less susceptible to degradation by cellular mechanisms than macromolecules; and (iv) they are not as apt to elicit an immune response as macromolecules. In addition, many pharmaceutical companies have extensive libraries of chemical compounds and/or biological mixtures, often fungal, bacterial, or algal extracts, that would be desirable to screen with the assay of the present invention.

Several classes of small molecules that interact with double-stranded DNA have been identified, and a number of small DNA-binding molecules have been shown to preferentially recognize particular types of nucleotides sequences (e.g., AT-rich regions) and/or specific nucleotide sequences. Such molecules can be tested in the assay of the invention to determine the constraints on sequences flanking these known recognition sequences to identify preferred or optimal binding sites. Initial information on the sequence-dependent binding activity of a candidate compound can also be predicted from the structure of the candidate compound and/or obtained in a conventional pre-screening assay. Nucleic acid molecule(s) useful for assaying compound binding can then be designed to include preferred types of nucleotide sequences or preferred specific sequences in the first region that target the candidate compound to the first region, as described above.

Accordingly, the candidate compound preferably contains, as part of its structure, or is modified to contain, a moiety that binds preferentially or specifically to a target nucleotide sequence in the first region. Generally, this target nucleotide sequence represents a portion of the preferred or optimal binding site, which may, for example be on the order of about 5 to about 25, preferably about 5 to about 20, and more preferably about 5 to about 10, nucleotides in length. The remainder of the preferred or optimal binding site is generally included in the adjacent second region of the nucleic acid molecule.

If the binding site for a given candidate compound includes the site in the first region that is susceptible to modification, the structure of that site preferably does not interfere with compound binding. Thus, if a non-standard nucleotide makes up part of the binding site for the candidate compound, the presence of the non-standard nucleotide does not significantly interfere with binding of the compound to the nucleic acid molecule.

In exemplary embodiments, DNA-binding moieties such as distamycin and netropsin, or other compounds known to bind preferentially to tetrameric AT-rich sequences (such as 5'-AAAA-3'/3'-TTTT-5') can be used as an integral part of the test compound, or an adjunct moiety. Thus, for example to screen for compounds capable of binding preferentially to GC-rich regions, an AT-binding moiety can be dimerized with the putative GC-binding compounds of interest, forming a dimer that can bind to an AT-rich sequence in the first region of the nucleic acid molecule and a GC-rich sequence in the adjacent second region. Conversely, to screen for compounds capable of binding preferentially to AT-rich regions, a GC-binding moiety can be dimerized with the putative AT-binding compounds of interest, forming a dimer that can bind to nucleic acid molecules having a GC-rich first region and an adjacent AT-rich second region.

Candidate compounds are selected for use in the invention based on sequence-preferential or sequence-specific binding, binding affinity, and the ability to block nucleic acid modification by a modifying agent. Those of skill in the art can readily design suitable candidate compounds for use in a particular application of the invention, if necessary, conducting preliminary assays to identify appropriate combinations of nucleic acid sequences, candidate compounds, and modifying agents for particular applications.

Examples of candidate compounds suitable for use in the nucleic acid binding assay described herein include, but are not limited to, DNA- or RNA-binding compounds (e.g., linear or cyclized dimers or multimers of known DNA-binding compounds), peptide nucleic acids (PNAs), polyamides, various triplex forming DNA-binding compounds, and derivatives thereof.

PNAs are compounds that are analogous to oligonucleotides, but differ in composition. In PNAs, the deoxyribose backbone of oligonucleotide is replaced by a peptide backbone. (See, e.g., Hanvey et al., 1992; Egholm, M. et al., 1992; Peffer, N. J. et al., 1993; Wittung, P. et al., 1994).

Exemplary polyamides include N-methylpyrrole and N-methylimidazole amino acids that act as synthetic DNA ligands that bind to predetermined sequences in the minor groove of DNA. (See, e.g., McBryant S J et al., 1999; Bremer R E et al., 1998; and White S et al., 1997.)

Exemplary triplex forming DNA-binding compounds include the aromatic diamidine, DAPI (4',6-diamidino-2-phenylindole), which can induce the formation of an RNA-DNA hybrid triplex (Xu Z et al., 1997); homopyrimidine PNAs which have been shown to bind complementary DNA or RNA, forming $(PNA)_2$/DNA(RNA) triplexes (Egholm et al., 1991); nucleic acid analogs such as methylphosphonates and phosphorothioates (Miller, et al., U.S. Pat. No. 4,757,055, issued Jul. 19, 1988); and other small intercalating agents coupled to oligonucleotides (Montenay-Garestier T., et al., 1991). Duplex-binding polynucleotide analogs with morpholino-sugar backbones, disclosed in U.S. Pat. No. 5,405,938, are also contemplated.

Although exemplary classes of compounds are described herein, it will be understood that any candidate compounds that exhibit nucleotide sequence-dependent binding are of interest in practicing the invention described herein.

In some cases, candidate compounds can be initially identified as monomers; however, such monomers may be modified, dimerized, and/or cyclyzed for use in the nucleic acid binding assay, as described above. In addition, a candidate compound can be modified, e.g., after an initial round of testing in the assay of the invention, to improve any of a number of properties, including binding affinity, transcriptional regulatory protein displacement activity, solubility, pharmacokinetics, side effects or toxicity, and production cost. The assay of the invention can then be used to test the impact of such modifications on the specificity and affinity of binding.

By way of example, a compound designated "21x" has been identified that binds to an 8 to 10 base pair stretch of AT-rich double-stranded DNA. 21X is a dimer of netropsin, which is known to bind to the minor groove of DNA and accordingly was predicted to interact with double-stranded DNA through minor groove contacts. A detailed biochemical characterization of 21x is provided in co-owned U.S. Ser. No. 60/154,415, which is expressly incorporated by reference herein.

Binding of Ligand(s) to Nucleic Acid Molecule(s)

The nucleic acid binding assay entails contacting the nucleic acid molecule(s) being tested with the candidate ligand(s), under conditions suitable for sequence-dependent binding of the ligand to the nucleic acid molecule. Suitable conditions will depend on the type of ligand, the nucleotide sequence of the binding site, and the desired "affinity threshold" for the binding interactions to be tested. The "affinity threshold" can, for example, be low, in which case, binding conditions allow low- as well as high-affinity binding, and the sequence requirements of all of these binding interactions are assayed. Preferably, however, the affinity threshold is high, in which case binding conditions favor high-affinity binding, and the sequence requirements of high-affinity binding are assayed. The parameters that affect the binding of particular pairs of nucleic acid molecules and candidate ligand types are known to those of skill in the art, and suitable conditions for binding the candidate ligand to the nucleic acid(s) can readily be determined by those of skill in the art in light of the guidance herein. For example, temperature, pH, and salt conditions are well-known to influence binding interactions, as are the relative concentrations of ligand and cognate binding site(s). If a high affinity threshold is desired, the ligand concentration, for example, can be relatively low with respect to the concentration of nucleic acid binding sites.

The binding conditions should generally be selected to promote the formation of a sufficiently stable ligand/nucleic acid complex that nucleic acid molecules having a ligand bound to the second region are substantially protected from modification at the susceptible site in the first region, and nucleic acid molecules wherein a ligand is not bound to the second region are substantially modified at this site. Preferably, the binding affinity of this interaction is relatively high, with a $K_d$ on the order of, e.g., about 10 micromolar ($\mu$M), about 1 $\mu$M, about 100 nanomolar (nM), about 10 nM, about 1 nM, about 100 picomolar (pM), about 10 pM, or about 1 pM. As described below, the assay of the invention can include a determination of the $K_d$ of the binding interaction between a ligand and nucleic acid molecule.

In a preferred embodiment, a set of different nucleic acid molecules, preferably in which each molecule has a different nucleotide sequence in the second region, is assayed to obtain information about the sequence preferences of a ligand. For example, in a preferred embodiment, the ligand's binding site spans the first and second regions, and the nucleic acid molecules include an invariant nucleotide sequence in the first region to target the ligand to the binding site and a variable nucleotide sequence in the second region to determine preferred or optimal binding sites (i.e., those for which binding is specific and relatively high affinity). In this embodiment, binding conditions are generally selected so that the ligand binds to some, but not all, of the nucleic acid molecules in the set. The conditions can be set to assay for high-affinity binding, as described above.

Modification of Unbound Nucleic Acid Molecule(s)

After contacting the ligand(s) with the nucleic acid molecule(s), the resultant reaction mixture is treated with a modifying agent, under conditions wherein ligand-bound nucleic acid molecules are substantially protected from modification at the susceptible site, and unbound nucleic acid molecules are substantially modified at this site. As used in the context, the term "substantially" is intended to indicate a degree of protection from modification for bound molecules and a degree of modification for unbound molecules sufficient to allow detectable amplification of protected molecules over any background level of amplification associated with the assay.

In a preferred embodiment employing a double-stranded nucleic acid, the susceptible site is on the first strand, and amplification of the second strand is blocked by modification of an additional site in an upstream region of the second strand (see above). Preferably, a single modifying agent can modify both sites. However, two modifying agents, one specific for each site can also be employed. If the reaction conditions for the two agents are compatible, the modifications can be carried out simultaneously in the same reaction mixture. Alternatively, the modifications can be carried out sequentially, with removal or inactivation of reaction components and addition of new components, as appropriate.

Modifying agents suitable for use in the invention include any agent that can modify a susceptible site in a nucleic acid molecule, wherein such modification can be blocked by the sequence-dependent binding of a candidate ligand to the nucleic acid molecule. Preferred modifying agents include enzymes. A variety of prokaryotic and eukaryotic enzymes, whose function is to recognize and remove non-standard bases from duplex DNA or DNA/RNA duplexes, either by cleaving the non-standard nucleotide backbone or excising the nucleotide bases are suitable, where the nucleic acid molecule(s) are double-stranded, and the first region of the first strand includes a non-standard nucleotide recognized by the enzyme.

By way of example, uracil DNA glycosylase (UDG) catalyses the removal of uracil from double-stranded DNA producing abasic residues and may be used to render unprotected sequences incapable of amplification. The UDG enzyme has been well characterized, e.g., Luo, N. Biochemistry, (1999) 38(29):9209, and thermostable UDG enzymes, such as described by Sandigursky, M., et al., Curr Biol (1999), 9(10):531, can be employed, allowing the assay to be carried out at elevated temperature, if desired. Also, it has previously been shown that UDG can be used as a footprinting reagent to "footprint" target sequences with DNA binding compounds.

UDG finds utility in the methods described herein due to the fact that many candidate compounds contain pyrrole carboxamide cores, which prefer A/T base pairs, and it is possible to use a short A/T stretch in double-stranded nucleic acid molecules to direct a candidate compound to the target binding site.

In one example, a target binding site for candidate compound binding is represented by an A/T anchoring sequence portion plus a flanking sequence which consists of variable, e.g., combinatorial sequences. The T residues in the A/T stretch can be substituted by uracil, and this conveniently provides a means for the uracil-containing site to be modified (i.e., destroyed) by UDG when the site is not protected by a bound compound. When uracil removal takes place, the abasic regions are not elongated during amplification by primer-directed polymerization, e.g., PCR.

In addition, UDG locates target uracil residues by scanning the minor groove of double-stranded DNA and is therefore susceptible to inhibition by compounds that bind to the minor groove of DNA. Thus, UDG is particularly useful in assays designed to screen compounds for sequence-dependent minor groove binding.

As another example, the repair enzyme FPG (formamidopyrimidine or 8-oxoguanine DNA glycosylase) can be employed as the modifying enzyme, where the first region of the nucleic acid molecule(s) includes a non-standard nucleotide, such as a formamidopyridine residue, e.g., 2,6-diamino-4-hydroxyl-5-methylformamidopyrimidine, or 8-oxoguanine. (Ischenko A A, et al., J Biomol Struct Dyn (1999) 17(2):301.)

As still another example, the repair endonuclease III from *E. coli* can be employed as the modifying enzyme, where the non-standard base in one strand of the duplex target first region is thymine glycol (D'Ham, C., et al., Biochemistry (1999), 38:11:3335.)

A restriction enzyme can also be employed as a modifying enzyme in the assay, where the nucleic acid molecule(s) are double-stranded, and the first duplex region includes a site cleaved by the restriction enzyme. A wide variety of suitable restriction enzymes are commercially available, and the reaction conditions for such enzymes are well known. In particular, type IIS restriction enzymes, which recognize asymmetric sequences and generally cleave a few nucleotides away from the recognition sequence, can be employed in the present invention in a manner analogous to UDG (see Example 1). For example, the type IIS enzyme BceAI, recognizes the sequence ACGGG and cleaves at a site that is 12 nucleotides downstream from the 3' end of this sequence on the upper strand and 13 bases downstream on the lower strand. Other exemplary type IIS restriction enzymes suitable for use in the invention include BsgI, BslI, BsmBI, FokI, HgaI, and the like.

Amplication of Unmodified Nucleic Acid Molecule(s)

After treatment of the reaction mixture with one or more modifying agents, the modifying agent(s) are preferably removed or inactivated, and the nucleic acid molecule(s) are contacted with a polymerase enzyme. The polymerase and reaction conditions are such that only unmodified nucleic acid strands are amplified, so that the amplification indicates that a ligand binds to a nucleotide sequence in said second region.

Amplification is conveniently carried out by primer-directed polymerase chain reaction (PCR), according to standard techniques. Where the nucleic acid molecules in the reaction mixture are initially double-stranded, the nucleic acid strands are first denatured, cooled to anneal with added primers, and then copied by primer-directed polymerization, preferably using a thermo-stable polymerase, as is well known.

As stated above, double-stranded nucleic acid molecules preferably include a non-standard nucleotide in the second strand, upstream of the first and second regions. An important feature of this embodiment is that UDG treatment will destroy the upper strand regardless of whether a compound binds to nucleic acid molecule, so that even if the susceptible site in the first region is fully protected by high-affinity binding of a compound, PCR amplification will result in a amplification product level no more than half of that of a sample without UDG treatment.

Where the assay is performed to screen a set of different nucleic acid molecules with variable second-region nucleotide sequences, and the ligand binds to a relatively large percentage of these sequences (e.g., all those that are GC-rich) the amount of material amplified may be sufficient for direct isolation of the amplified material, followed by nucleotide sequencing to determine sequence preferences. On the other hand, to identify binding that involves very high sequence specificity, i.e., where relatively few nucleic acid molecules in the set include preferred sequences, it may be necessary to carry the screening process through two or more cycles, where each cycle involves compound binding, treatment with a modifying agent, and amplification. If the nucleic acid molecules include non-standard nucleotides in the susceptible site on the first strand and in an upstream location on the second strand, these non-standard nucleotides can be maintained in molecules through multiple rounds of selection by designing the PCR primers to introduce non-standard nucleotides into appropriate positions in the amplification products.

If a compound shows little or no preference for particular sequence(s) in the variable second region, the assay will yield a nucleotide sequence corresponding to the amplified strand that that shows relatively equal amounts of each of the four bases at each position in the variable region.

Compounds that show sequence preference in the variable second region yield an amplification product that shows a significantly higher level of preferred nucleotides at each position than the level of other nucleotides. For example, the compound 21X (see below) is shown to have AT-rich sequence preference by the fact that the observed sequences in the variable region of the amplified strands are high in A and T and low in G and C. If a significant percentage of the total variable target sequences are AT-rich, this result can be observed by sequencing strands after a single round of compound binding, modification, and amplification.

A compound that has high sequence specificity for nucleic acid binding will yield an amplification product that shows high levels for specific bases at one or more positions in the variable second region of the nucleic acid molecules.

Those of skill in the art understand that the levels of a given nucleotide at particular position are assessed by comparison with the level for that nucleotide at that position when the assay is carried out in the absence of candidate compound. As those of kill in the art appreciate, a background level of amplification is typically observed, due to he ability of some unbound nucleic acid molecule to escape modification by the modifying agent, combined with the very high amplification capability of techniques such as PCR. In studies conducted in connection with the present invention, for example, the amount of material amplified in the absence of compound is about $\frac{1}{30}$ of that which is amplified when the nucleic acid molecules are not modified.

In a preferred embodiment, the amplification reaction can include an oligonucleotide to prevent re-annealing of non-amplified products. In the embodiment illustrated below, the TaqMan™ probe serves this purpose.

In addition, to quantitate the level of amplification, oligonucleotide probes such as the TaqMan™ probe can be constructed such that they include fluorescent and quenching components. When the TaqMan™ probe is intact, the fluorescence is quenched due to the proximity of the quencher. However, since Taq DNA polymerase has a 5' to 3' exonuclease activity, TaqMan™ probes designed to anneal to targets between the two PCR primers are degraded during the course of PCR. This will cause an increase in fluorescence as the number of PCR cycles increases. The amount of the fluorescence is directly proportional to the amount of PCR product synthesized and can therefore be used for quantitation purposes.

In the UDG assay describe below, for example, TaqMan™ analysis reveals that UDG digestion typically causes about a 30-fold reduction in the amount of template available for PCR amplification. Addition of a compound capable of blocking the effects of UDG interferes with this reduction in a manner that is dependent on the binding affinity of the compound, the compound's specificity (i.e., whether the compound can bind to a small or large number of the nucleotide sequences present), and the number of rounds of compound binding, modification, and amplification that have been carried out. Compounds that have little or no binding activity fail to relieve the reduction in the amount of template available for PCR. The degree of protection with UDG treatment is dependent upon the affinity of binding of a candidate compound for the nucleic acid molecule. A given candidate compound that binds to different nucleic acid molecules in the reaction mixture with varying affinities, will result in varying levels of protection upon UDG treatment. Accordingly an evaluation of the sequencing results of PCR-amplified products, taken together with any known sequence preference of the candidate compound, facilitates identification of optimal compound/binding sequence sites.

Determination of Ligand Binding Affinity

The nucleic acid binding assay of the invention can also be employed to determine the affinity with which a ligand bind to a nucleic acid molecule. In particular, the dissociation constant ($K_d$) for the binding interaction can be determined by measuring concentration of ligand that protects approximately 50 percent of the first-region susceptible sites from modification. This concentration can be measured by performing the assay described herein and including a "reference" reaction in which the nucleic acid molecule is amplified without prior exposure to ligand or modifying agent. This provides a measurement of the amount of template available for amplification. Treatment of the nucleic acid molecule with a modifying agent reduces the amount of available template, and ligand-binding protects the nucleic acid molecule from modification, which preserves template for amplification.

If quantitative amplification is carried out, differences in available template can be detected as a difference in the number of cycles required to generate a threshold level of amplification product. To estimate $K_d$, therefore, quantitative amplification, preferably, PCR, is performed and the threshold cycle (Ct) value is determined for both the test and reference reactions. The degree to which the Ct value for the test reaction increases, compared to the reference reaction, provides an indication of binding affinity (i.e., a smaller increase in Ct value indicates a higher binding affinity and vice versa).

To determine $K_d$, the assay is preferably carried out under conditions where only one strand corresponding to the nucleic acid molecule can be amplified. Thus, the nucleic acid molecule is preferably single-stranded or is a double-stranded nucleic acid designed so that only the first strand containing the site that is susceptible to modification can be amplified (i.e., because the second stand is always rendered incapable of amplification because it is modified by treatment with a modifying agent). In the latter case, the reference reaction might yield, for example, a Ct value of 16. Because modification of the second strand prevents its amplification, maximal protection of the susceptible site on the first strand would correspond to a Ct value of 17. Accordingly, half-maximal protection of this site would correspond to a Ct value of 18. Thus, $K_d$ is estimated by determining the concentration of ligand that gives a Ct value about 2 higher than the Ct value obtained when the nucleic acid molecule is amplified without prior exposure to ligand or modifying enzyme.

To estimate $K_d$ by this method, it is generally preferable to perform the assay with multiple test reaction mixtures that contain different concentrations of ligand, in addition to including a negative control. The Ct values for different ligand concentrations can, if desired, be graphed (with ligand concentration on the x-axis and Ct value on the y-axis) to give a curve which can be used determine the ligand concentration that reduces Ct value by one, if this reduction is not achieved with one of the concentrations tested in the assay. Alternatively, the Ct value can be converted to relative copy number and graphed (with ligand concentration on the x-axis and Ct valued on the y-axis) to give a dose-response curve. The $K_d$ is equal to the compound concentration that gives the half-maximal increase in relative copy number.

II. Nucleic Acid Binding Selection Method

The nucleic acid binding assay of the method can also be used in a novel nucleic acid binding selection method whereby ligands and the nucleic acid molecules to which they bind can be simultaneously selected. This "co-selection" method can be used, for example, to identify transcription factors with a particular binding characteristic, e.g., minor groove-binding, and the nucleotide sequences to which they bind. This information can then be used to identify genes with promoters containing such nucleotide sequences as putative targets for therapies that rely on minor-groove binding compounds to regulate gene transcription.

In General

The nucleic acid binding selection method of the invention uses the strategy described above to selectively amplify ligand-binding nucleic acid molecules from a set of candidate nucleic acid molecules. In addition, the ligands that bind are separated from non-binding ligands in a set of candidate ligands and recovered.

Sets Nucleic Acid Molecules

Sets of nucleic acid molecules suitable for use in the selection method are as described above for the binding assay. More specifically, the nucleic acid molecules have a first region and an adjacent second region. The first region contains a first site that is susceptible to modification by a modifying agent, and the second contains a variable sequence component.

In preferred embodiments, the nucleic acid molecules are linked to a substrate to facilitate separation of ligands bound to the nucleic acid molecules from unbound ligands. The substrate preferably has a low capacity for non-specific binding to proteins under the selection conditions. A variety of suitable substrates are known for use in conventional affinity purification techniques and can be employed as a substrate in the present selection methods. Examples include agarose beads, acrylamide beads, glass beads, cellulose, various acrylic copolymers, hydroxyalkyl methacrylate gels, polyacrylic and polymethacrylic copolymers, nylon, neutral and ionic carriers, and the like.

The nucleic acid molecules can be linked to the substrate by any linkage that does not interfere with the sequence-dependent binding of ligand to the nucleic acid molecules. The linkage can be covalent or non-covalent. The nucleic acid molecules can include a non-nucleotide moiety to facilitate linkage to the substrate. For example, the nucleic acid molecules can be biotinylated for attachment to an avidin-coated substrate. Double-stranded nucleic acid molecules can be linked to the substrate via one or both strands. Linkage via one strand can be achieved, for example, by synthesizing oligonucleotides including a linking moiety and annealing these oligonucleotides with complementary oligonucleotides that lack the linking moiety. In a preferred embodiment, the linkage is a reversible linkage, which allows the nucleic acid molecules to be released from the substrate. Biotinylated nucleic acid molecules, for example, can be eluted from the substrate using an avidin-containing solution.

Sets of Ligands

The selection method can be performed using any type of ligand suitable for use in the binding assay of the invention. In a preferred embodiment, the set of ligands is collection of heterologous peptides expressed on the surface of phage particles produced from a phage display library, and the selection method is carried out in a manner analogous to conventional phage display selection. This embodiment offers the advantage that phage particles bearing nucleic acid-binding peptides contain the DNA that encodes such peptides. This DNA can then be sequenced to identify the peptides that bind to the nucleic acid molecules of the invention. For ease of description, the selection method is described in detail below with reference to this embodiment; however, those of skill appreciate that other types of ligands can be selected using standard techniques.

Production of a Phase Display Library

The ability to express heterologous peptides on the surface of viruses that infect bacteria (bacteriophage or phage) makes it possible to isolate a single nucleic acid-binding peptide, corresponding to a cloned DNA sequence, e.g., from a library of greater than $10^{10}$ nonbinding clones. To express peptides on the surface of phage (phage display), a nucleotide sequence encoding the peptide is inserted into the gene encoding a phage surface protein (e.g., pIII) and the peptide-pIII fusion protein is displayed on the phage surface (McCafferty et al. (1990) Nature, 348: 552–554; Hoogenboom et al. (1991) Nucleic Acids Res. 19: 4133–4137).

Phage particles bearing nucleic acid-binding peptides can be separated from non-binding phage particles by affinity chromatography (McCafferty et al. (1990) Nature, 348: 552–554). Depending on the affinity of the peptide, enrichment factors of about 20-fold to about 1,000,000-fold are obtained for a single round of affinity selection. By infecting bacteria with the eluted phage, however, more phage can be grown and subjected to another round of selection. In this way, an enrichment of about 1000-fold in one round can become about 1,000,000-fold in two rounds of selection (McCafferty et al. (1990) Nature, 348: 552–554). Thus even when enrichments are low (Marks et al. (1991) J. Mol. Biol. 222: 581–597), multiple rounds of affinity selection can lead to the isolation of rare phage.

Any phage display library can be employed in the selection method of the invention. Phage display libraries useful in the invention can display, for example, substantially full-length natural (i.e. "native" or "wild-type") polypeptides or fragments thereof, as well as amino acid variants thereof. Such polypeptides can be derived from any cell or tissue and from any organism. If desired, libraries useful in the invention can be derived from a diseased (e.g., cancerous) cell tissue and/or from a cell or tissue that has been treated with an agent that induces the expression of particular genes. In preferred embodiments, the library is derived from a mammalian cell or tissue, and more preferably from a human cell or tissue.

Heterologous peptides for display on the surface of a phage preferably include a rigid secondary structure. For peptides derived from a natural protein (e.g., a transcription factor), the rigid secondary structure is one that is exposed on the surface of the protein. In this context, the phrase "rigid secondary structure" refers to any polypeptide segment exhibiting a regular repeated structure such as is found, e.g., in alpha-helices, parallel and antiparallel beta-sheets, and reverse turns. Certain "non-ordered" structures that lack recognizable geometric order are also included in the definition of rigid secondary structure provided they form a domain or "patch" of amino acid residues capable of interaction with a target. Of course, those of skill in the art understand that a phage display library can include peptides that do not include such a structure, in which case, the phage bearing such peptides are generally eliminated during the selection process.

Phage display libraries are contructed by inserting nucleic acids encoding the desired heterologous peptides into a suitable phage vector. Nucleic acids encoding the heterologous peptides can be isolated by known methods for purifying nucleic acids (see generally, Sambrook et al., Molecular Biology: A Laboratory Manual, Cold Spring Harbor Press, Cold Spring Harbor, N.Y. 1989). In addition, phage display libraries can also be constructed from amplified nucleic sequences, such as those produced by PCR, as described in section 14 of Sambrook et al., supra. Nucleic acids can also be chemically synthesized (Merrifeld, J. Am. Chem. Soc., 85:2149, 1963).

After nucleic acids encoding heterologous peptides have been obtained, the nucleic acids are inserted into a suitable phage display vector (preferably a plasmid) using recombiant techniques, as described generally in Sambrook et al., supra. The nucleic acids are inserted into the vector upstream of a gene encoding a phage coat protein, typically the M13 gene III coat protein. The resulting constructs express the heterologous peptides as fusions with the phage coat protein.

While several types of vectors are available and can be used to practice this invention, plasmid vectors are the preferred vectors for use herein, as they may be constructed with relative ease, and can be readily amplified. Plasmid vectors generally contain a variety of components including promoters, signal sequences, phenotypic selection genes, origin of replication sites, and other necessary components as are known to those of ordinary skill in the art. Promoters most commonly used in prokaryotic vectors include the lac Z promoter system, the alkaline phosphatase pho A promoter, the bacteriophage lambda PL promoter (a temperature sensitive promoter), the tac promoter (a hybrid trp-lac promoter that is regulated by the lac repressor), the tryptophan promoter, and the bacteriophage T7 promoter. For a general descriptions of promoters, see section 17 of Sambrook et al. supra. While these are the most commonly used promoters, other suitable microbial promoters may be used as well.

Preferred promoters for practicing this invention are those that can be tightly regulated such that expression of the fusion gene can be precisely controlled. Regulating expression of the heterologous peptide-coat protein fusion so that no more than a minor amount, i.e. fewer than about 1%, of the phage particles contain multiple copies of the fusion protein, facilitates selection of high affinity polypeptides. Thus, depending on the promoter, culturing conditions of the host are adjusted to maximize the number of phage particles containing a single copy of the fusion protein and minimize the number of phage particles containing multiple copies of the fusion protein. Preferred promoters used to practice this invention are the lac Z promoter and the pho A promoter.

The vector preferably includes a signal sequence, which is typically located immediately 5' to the gene encoding the fusion protein, and will thus be translated at the amino terminus of the fusion protein. Suitable prokaryotic signal sequences may be obtained from genes encoding, for example, LamB or OmpF (Wong et al., Gene, 68:193 (1983)), Ma1E, PhoA and other genes. A preferred prokaryotic signal sequence for practicing this invention is the *E. coli* heat-stable enterotoxin II (STII) signal sequence as described by Chang et al., Gene, 55:189 (1987).

Another useful component of the vectors used to practice this invention is phenotypic selection genes. Typical phenotypic selection genes are those encoding proteins that confer antibiotic resistance upon the host cell. By way of illustration, the ampicillin resistance gene (amp), and the tetracycline resistance gene (tet) are readily employed for this purpose.

Construction of a suitable phage display library comprising the aforementioned components as well as the genes encoding the fusion polypeptides can be carried out using standard recombinant DNA procedures as described in Sambrook et al. supra. Isolated DNA fragments to be combined to form the vector are produced and ligated together in a specific order and orientation to generate the desired vector.

The library thus produced is typically introduced into a suitable host cell. Any host cell suitable for use with the particular vector can be employed, but prokaryotes are the preferred host cells for this invention. Suitable prokaryotic host cells include *E. coli* strain JM101, *E. coli* K12 strain 294 (ATCC number 31,446), *E. coli* strain W3110 (ATCC number 27,325), *E. coli* X1776 (ATCC number 31,537), *E. coli* XL-1Blue (stratagene), and *E. coli* B; however many other strains of *E. coli*, such as HB101, NM522, NM538, NM539, and many other species and genera of prokaryotes may be used as well. In addition to the *E. coli* strains listed above, bacilli such as *Bacillus subtilis*, other enterobacteriaceae such as *Salmonella typhimurium* or *Serratia marcesans*, and various Pseudomonas species may all be used as hosts.

Any available method can be used to introduce the phage display library into the host cells. Transformation of prokaryotic cells is readily accomplished using the calcium chloride method as described in section 1.82 of Sambrook et al., supra. Alternatively, electroporation (Neumann et al., EMBO J., 1:84, 1982) can be used to transform these cells. The transformed cells are generally selected by growth on an antibiotic (e.g., tetracycline or ampicillin) to which they are rendered resistant due to the presence of tet and/or amp resistance genes on the vector. Phage particles are produced by culturing the host cells in the presence of a helper phage (i.e., typically one that facilitates excision and packaging of the viral DNA) and recovering the phage particles from the culture medium.

Binding and Modification of Nucleic Acid Molecules

The selection method of the invention entails contacting the set of nucleic acid molecules with the set of different ligands, under conditions suitable for sequence-dependent binding of one or more ligands to one or more of the nucleic acid molecules. The resultant reaction mixture is then treated with a modifying agent, as described above.

Where the set of ligands is provided by a phage display library, the nucleic acid molecules are preferably linked to a substrate. The immobilized nucleic acid molecules are contacted with the library of phage particles under conditions suitable for sequence-dependent binding of one or more of the phage particles. Preferably, the conditions, including pH, ionic strength, temperature and the like will mimic physiological conditions.

Binding is followed by treatment with a modifying agent, under conditions wherein ligand-bound nucleic acid molecules are substantially protected from modification at the susceptible site, and unbound nucleic acid molecules are substantially modified at this site. In a preferred embodiment employing a double-stranded nucleic acid, the susceptible site is on the first strand, and the second strand includes an additional modification site in an upstream region of the second strand to prevent amplification of the second strand (see above). Preferably, a single modifying agent can modify both sites. However, two modifying agents, one specific for each site can also be employed. If the reaction conditions for the two agents are compatible, the modifications can be carried out simultaneously in the same reaction mixture. Alternatively, the modifications can be carried out sequentially, with removal or inactivation of reaction components and addition of new components, as appropriate. Any modifying agent useful in the nucleic acid binding assay described herein can also be used in the nucleic acid binding selection method of the invention. Preferably, modifying enzymes, such as repair enzymes or restriction enzymes, are employed. Examples of suitable repair enzymes include UDG, FPG, and endonuclease III. After modification, the modifying enzyme is generally removed or inactivated to prevent modification of nucleic acid molecules after recovery of bound ligands.

Recovery of Bound Ligands

Ligands that bind to the nucleic acid molecules are separated from unbound ligand by conventional methods, such as, for example, those used in affinity purification. If the nucleic acid molecules are linked to substrate, the substrate can simply be washed to remove unbound ligands and ligands that bind in a non-sequence dependent manner or with low affinity. The bound ligands can then be eluted off the substrate and recovered. "Binders" can be dissociated from the immobilized nucleic acid molecules by any of a variety of well-known methods, including altering pH and/ or ionic strength. The recovered ligands represent a pool of selected ligands that bind in a sequence-dependent manner to one or more nucleotide sequences present in the nucleic acid molecules.

Where the ligands are provided by a phage display library, a pool of selected phage particles is obtained, which, together with helper phage, can be used to infect suitable host cells. The infected host cells can then be cultured under conditions suitable for amplification of the phage particles to produce phage particles for an additional round of selection, if desired (see below).

Amplication of Unmodified Nucleic Acid Molecules

After removal or inactivation of the modifying enzyme, and preferably after the recovery of bound ligands, the unmodified nucleic acid molecules, i.e., those that were protected from modification by bound ligand, are amplified, as described above for the nucleic acid binding assay. Thus, the nucleic acid molecules are contacted with a polymerase under conditions wherein only unmodified nucleic acid strands are amplified, preferably via primer-directed PCR.

Amplification can be carried out with the nucleic acid molecules linked to a substrate, if desired, provided the substrate linkage does not interfere with the amplification reaction. If amplification is by PCR, for example, the primer sites in the substrate-linked nucleic acid molecules must be accessible to the primers. Alternatively, the nucleic acid strands to be amplified can be released from the substrate and amplified in solution. In this embodiment, the nucleic acid strands are preferably linked to the substrate by a reversible linkage, and the strands are treated with an appropriate agent to effect release. When double-stranded nucleic acid molecules are employed, both strands can be released, followed by selective amplification of the first strand, which contains the site that is susceptible to modification. In this embodiment, selective first-strand amplification can be achieved, for example, by including an additional modification site in an upstream region of the second strand to prevent amplification of the second strand. In an alternative embodiment, linkage of the double-stranded nucleic acid molecules to the substrate via the second strand can be employed to facilitate selective amplification of the first strand. In particular, duplex nucleic acids linked via the second strand could be contacted with ligand, treated with modifying agent, and denatured to release the first strands from the substrate.

Amplification of unmodified nucleic acid strands produces a pool of selected nucleic acid molecules. This pool can be sequenced to determine the binding site preferences of the pool of selected ligands, as described above, and/or can be used in an additional round of selection.

Additional Round(s) of Selection

One or more additional round(s) of selection can optionally be carried to select ligand(s) having the desired affinity for the nucleic acid molecule(s).

For an additional round of selection via phage display, the pool selected phage particles is typically amplified by infection of host cells, followed by collection of the phage particles thus produced. The pool of selected nucleic acid molecules are preferably linked to a substrate, as described above. The phage particles are contacted with the pool of selected nucleic acid molecules under conditions suitable for sequence-dependent binding of one or more of the displayed heterologous peptides to one or more of the nucleic acid molecules. The resultant reaction mixture is treated with the appriopriate modifying agent(s), such that nucleic acid molecules having a heterologous peptide bound to the second region are substantially protected from modification at the susceptible site, and nucleic acid molecules that do not have a heterologous peptide bound to the second region are substantially modified at this site. The modifying agent is then removed or inactivated. The phage particles that bind via their heterologous peptides are then separated from unbound or loosely bound phage particles, and the binders are recovered. The unmodified strands of the nucleic acid molecules are amplified. Thus, a second round of selection yields a pool of twice-selected phage particles that bind in a sequence-dependent manner to one or more nucleotide sequences present in a pool of twice-selected nucleic acid molecules.

Additional rounds of selection can be carried out to select for ligands having increased affinity for the selected nucleic acid molecules. In addition, it is also possible to carry out a round of selection to select against ligands having affinity for an undesirable nucleotide sequence. The latter is advantageous, for example, to improve specificity for a particular target nucleotide sequence, as compared to particular non-target nucleotide sequence. To select against ligands that bind to the non-target nucleotide sequence, nucleic acid molecules having this sequence can be linked to a substrate, contacted with the ligands, and the non-binding ligands can be recovered.

Pools of Selected Ligands and Nucleic Acid Molecules

After the desired number of rounds of selection, the pools of selected nucleic acid molecules are typically sequenced to determine the binding site preferences of the selected ligands. Depending on the number of rounds of selection and on the enrichment for a particular binding pair in each round, the "pools" of selected ligands and nucleic acid molecules that are obtained may consist of one ligand and one, or a few, nucleic acid molecule(s) to which the ligand binds. In any case, the nucleic acid molecule(s) are generally sequenced to determine preferred or optimal sequences for the selected ligand(s).

This sequence information can then be compared to genomic DNA sequences to identify genes whose expression may be regulated by the binding of a transcription factor to a particular sequence. Thus, the selection method of the invention provides a means of identifying target genes for therapies based on transcriptional regulation. One advantage of this strategy is the ability to select for certain binding characteristics based on the choice of modifying agent. If, for example, one wishes to identify binding sites for transcription factors that bind to the minor groove of DNA, a modifying agent that binds to the minor groove would be employed in the selection method. Identifying such sites is of particular interest because compounds that bind to the minor groove can generally be made smaller than compounds that bind to the major groove. Thus, the selection method of the invention can be employed to identify those transcription factor binding sites that are the most viable targets for small-molecule therapeutics.

III. Nucleic Acid Binding Assay and Selection Kits

The invention also provides kits for use in performing the nucleic acid binding assay and selection method of the invention. A basic kit includes a set of nucleic acid molecules, each having a first region and a second region, adjacent to the first region. The first region of the nucleic acid molecules include a site that is susceptible to modification by a modifying agent, which modification blocks strand-directed duplication by a polymerase enzyme at said first site. In addition, the nucleic acid molecules include different nucleotide sequences in the second region. The set of nucleic acid molecules can include any of the above-described types of nucleic acid molecules. The set can be supplied in one or more solutions, i.e., as a mixture or in separate solutions. The set can also be supplied in dried, e.g., lyophilized, form. In either case, the set of nucleic acids is supplied in one or more containers. Alternatively, the set of nucleic acids can be supplied linked, preferably reversibly linked, to a solid substrate, which is typically enclosed in a container or other packaging material.

The basic kit also includes the modifying agent and, preferably, instructions for performing one or more of the methods described herein. The modifying agent can be any of the above-described modifying agents and is typically supplied in a container in solution or in dried form. The instructions can be affixed to the packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

In a preferred embodiment, the kit also includes primers that specifically bind to sites in the nucleic acid molecules that flank the first and second regions of the molecules. These primers are suitable for amplifying unmodified nucleic acid strands in the binding assay or the selection method of the invention.

In another preferred embodiment, the kit includes a pre-made phage display library. The library can be supplied in any convenient form, typically as a solution of phage, which can, together with helper phage, be used to infect an appropriate host cell. Suitable helper phage are preferably also included in the kit.

All patent and literature references cited in the present specification are hereby incorporated by reference in their entirety.

While the invention has been described with reference to specific methods and embodiments, it will be appreciated that various modifications and changes may be made without departing from the invention.

EXAMPLES

The following examples are offered to illustrate, but not to limit the claimed invention.

Example 1

Nucleic Acid Binding Assay

This example illustrates the nucleic acid binding assay of the invention.

Materials and Methods

Oligonucleotides

Top strand:
  TCT TGG CAG CAG GAU UGT CCU UGG ATC CAC TAC GCA GCG CCT CCC TCC
  ACT NNN NNN NNN AAA AGG GCT GGA GAC GTG GC
  (SEQ ID NO:1)
Bottom strand used for priming and PCR amplification:
  GCC ACG TCT CCA GCC CTT UU
  (SEQ ID NO:2)
Top strand for PCR amplification:
  TCT TGG CAG CAG GAU UGT CCU U
  (SEQ ID NO:3)

Oligonucleotide Fill in Reaction

Primers were first filled in using a buffer containing 10 mM Tris 8.3, 50 mM KCl, 1.5 mM $MgCl_2$, 0.001% gelatin ("PCR buffer"), and 200 mM each dNTP, 4 mg top strand, 2 mg bottom primer and 10 units Taq polymerase. The fill-in reaction proceeded with a 95 degree treatment for 10 minutes, followed by 3 minutes at 60 degrees, and 15 minutes at 72 degrees in a 100 ml reaction volume.

Binding Reaction

In a typical binding reaction, 2.6 ng filled-in oligonucleotide was incubated with from 5–20 nM DNA binding compound in PCR buffer (total volume 25 ml). Typically, 3 different compound concentrations were evaluated. Binding was allowed to proceed at room temperature for from 4 hours to overnight. Samples were then transferred to 37 degrees for 10 minutes. One unit of Uracil DNA Glycosylase (UDG) was then added and the digestion allowed to proceed for 3 minutes before it was stopped with an equal volume of 0.2% SDS. The reaction product was then diluted 250-fold with 0.2 mg/ml tRNA before proceeding to PCR.

PCR

PCR was carried out using standard procedures routinely employed in the art with 1X PCR buffer (25 ml reactions), 1.2 mM primers, 200 nM TaqMan™ probe, and 2 ml of the diluted UDG digestion mixture. TaqMan™ PCR proceeded for 27 cycles, where each cycle included 15 seconds at 95 degrees and 1 minute at 60 degrees, with the exception of first-cycle denaturation which took place for 10 minutes at 95 degrees.

Gel Purification

PCR products were gel-purified on 4% Nusieve GTG agarose gels. Quantitation of gel-purified PCR product for subsequent selection cycles was by TaqMan™ analysis against known standards.

TaqMan™

TaqMan™ analysis of PCR amplified products was performed for quantitation of UDG inhibition of PCR as well as quantitation of compound-mediated reversal of UDG inhibition.

The sequence of the TaqMan™ probe was:
AC TAC GCA GCG CCT CCC TCC ACT
(SEQ ID NO:4)

Assay and Results

Figure 4:
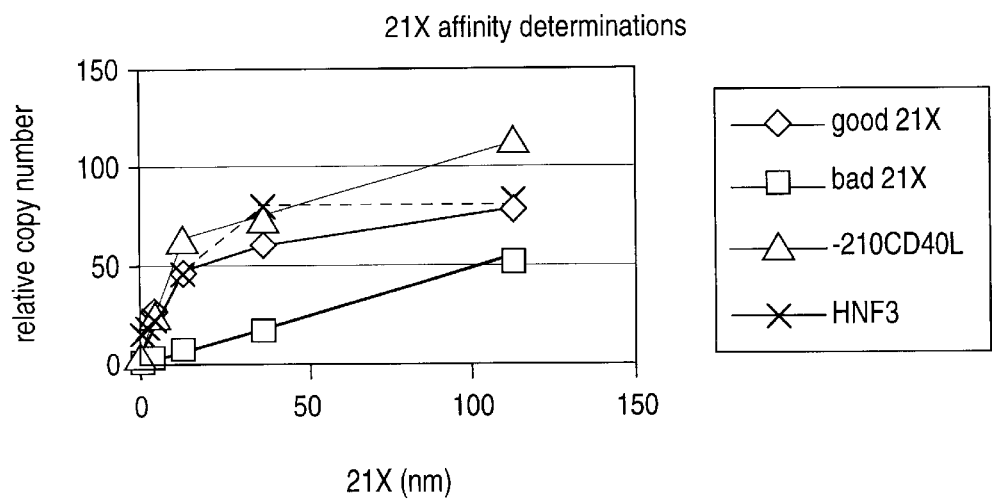
FIG. 4 shows the results of a nucleic acid binding assay of the invention in which the affinity of 21X for 4 different test duplex oligonucleotides was compared. In addition to an AT-rich ("good 21X") sequence and a GC-rich ("bad 21X") sequence, the assay included 121CD40L and HNF3 sequences (see Example 2). Relative copy number after amplification, calculated as described in Example 1, (y-axis) is shown for each 21X concentration tested (x-axis).
Figure 5A:
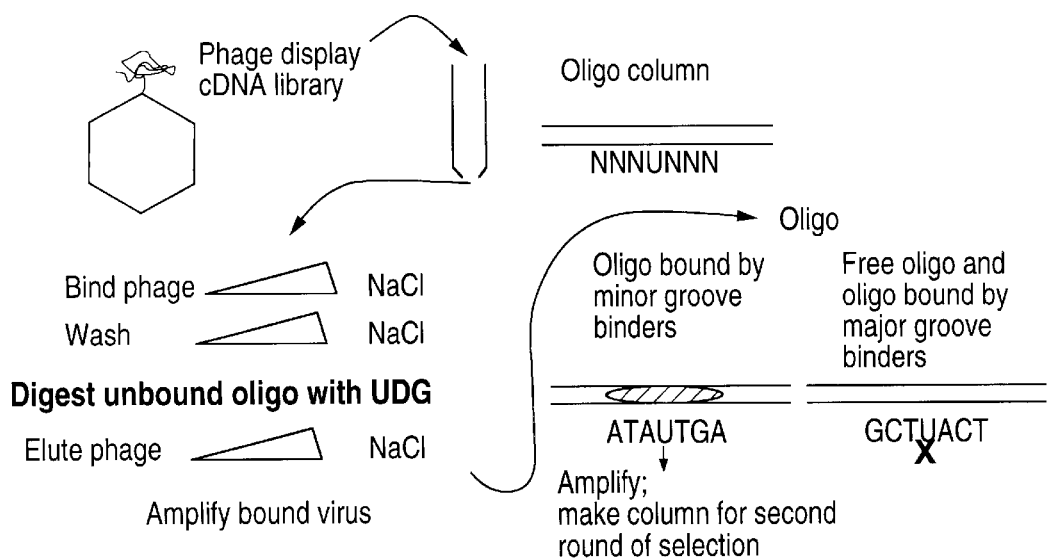
FIGS. 5A and 5B illustrate an embodiment of the nucleic acid selection method of the invention in which a phage display library provides ligands that are screened for binding to a column containing a set of oligonucleotides ("oligos") having a variable-sequence region. Unbound oligonucleotides are rendered incapable of amplification by treatment with uracil DNA glycosylase ("UDG"). Phage that bind are separated from unbound phage and recovered by elution. Oligonucleotides that were bound by phage are amplified, e.g., by polymerase chain reaction (PCR). An optional second round of selection can be carried out by preparing a second column from the amplified oligonucleotides and using the selected phage to infect host cells to produce additional selected phage (i.e., "amplifying" bound virus).
Figure 5B:
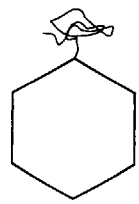
Figure 5B:
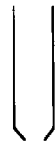

Duplex oligonucleotides (80 bp in length) were synthesized containing either non-preferred G/C-rich ("bad") or preferred AT-rich ("good") sequences for the AT-rich binding compound, 21x, at the target site (FIG. 4). Duplex oligonucleotides were incubated with (test samples) or without (control samples) 21x, treated with UDG to remove unprotected uracil residues and the resulting oligonucleotides amplified by RT-PCR.

The threshold cycle (Ct) value for each control sample (no UDG, no compound) was subtracted from the Ct value for each test sample to give ΔCt, then converted to copy number relative to the control by the following formula: relative copy number $2^{(-\Delta Ct)}$.

UDG treatment reduces the amount of DNA available for amplification by destroying both the upstream and the target sites with unprotected U. In the presence of 12.5 nM 21x, the amount of DNA containing the "good" site was dramatically increased while that containing the "bad" site was not affected. Since the theoretical maximum level of protection is 50, 21x was able to protect the target site to approximately 60% of maximum. These results show that the UDG-based binding assay can be used to determine optimal binding sequences for DNA binding compounds.

Example 2

Comparison of Nucleic Acid Binding Compound Affinity

This example illustrates the use of the nucleic acid binding assay of the invention to compare the binding affinity of the 21X ligand for different binding sites.

Materials and Methods

The materials and methods were essentially the same as described for Example 1, except that the following binding sites were assayed:

A "good" 21X site:

5'-TTTTAAAA-3'
3'AAAAUUTT-5'

A "bad" 21X site:

5'-CCGCAAAA-3'
3'-GGCGUUTT-5'

-210CD40L sequence:

5'-AAGAAGAAA-3'
3'-TTCUUCTTT-5'

HNF3core:

5'-TTCAAAGA-3'
3'-AAGTUUCT-5'

The -121CD40L and HNF3 sites are two representative cis-acting elements from promoters.

Assay and Results

The nucleic acid binding assay was carried out for each binding site essentially as described in Example 1. Ct values were measured and relative copy number calculated for each binding site. A graph of the results is shown in FIG. 4. The results indicate that 21 X, as expected, binds with relatively low affinity to the bad 21X site and with higher, and similar, affinity to the good 21X, -121CD40L, and HNF3 sites.

What is claimed is:

1. A method for screening a ligand for its ability to bind to a nucleotide sequence in a nucleic acid molecule, comprising:

(a) providing a nucleic acid molecule having a first region and second region, adjacent to said first region, wherein said first region comprises a first site that is susceptible to modification by a modifying agent, wherein such modification is effective to block strand-directed duplication by a polymerase enzyme at said first site;

(b) providing a ligand;

(c) contacting said nucleic acid molecule with said ligand, under conditions suitable for sequence-dependent binding of said ligand to said nucleic acid molecule, to form a reaction mixture;

(d) treating the reaction mixture of (c) with said modifying agent, under conditions wherein nucleic acid molecules comprising a ligand bound to said second region are substantially protected from modification at said first site, and nucleic acid molecules wherein a ligand is not bound to said second region are substantially modified at said first site;

(e) after said treatment, contacting said nucleic acid molecule with said polymerase enzyme, under conditions wherein only unmodified nucleic acid strands are amplified, wherein said amplification indicates that said ligand binds to a nucleotide sequence in said second region.

2. The method of claim 1, additionally comprising, after amplification of unmodified nucleic acid strands, repeating the contacting of (c), the treating of (d), and the contacting of (e), but substituting said amplification product for the nucleic acid molecule of (c)–(e).

3. The method of claim 1, wherein said providing of (a) comprises providing a set of different nucleic acid molecules that comprise different nucleotide sequences in said second region, and said method additionally comprises determining the nucleotide sequence of the amplification product in said second region to determine whether the ligand shows binding specificity for one or more nucleotide sequences in said second region.

4. The method of claim 1, wherein said nucleic acid molecule is a double-stranded nucleic acid molecule, said first and second regions are first and second duplex regions, said first site is on a first strand of said nucleic acid molecule, and said amplification comprises amplifying said first strand.

5. The method of claim 4, wherein said first site comprises a non-standard nucleotide that is modified by said modifying agent, wherein such modification is effective to block strand-directed duplication by said polymerase enzyme at said first site.

6. The method of claim 5, wherein said nucleic acid molecule comprises a second strand comprising one or more non-standard nucleotides that can be modified by the modifying agent, said treating is effective to modify the non-standard nucleotide(s) in the second strand, and said modifying agent is removed or inactivated prior to amplification of unmodified nucleic acid strands.

7. The method of claim 4, wherein said modifying agent is a restriction enzyme and said first site comprises a recognition site for said restriction enzyme.

8. The method of claim 7, wherein said nucleic acid molecule comprises a second strand comprising one or more non-standard nucleotides that can be modified by a different modifying agent, said treating additionally comprises treating said nucleic acid molecule with said different modifying agent to modify the non-standard nucleotide(s) in the second strand, and said different modifying agent is removed or inactivated prior to amplification of unmodified nucleic acid strands.

9. The method of claim 4, wherein the amplification of unmodified nucleic acid strands comprises primer-directed PCR amplification.

10. The method of claim 5, wherein the nucleic acid molecule comprises a DNA molecule, and the modifying agent is a prokaryotic or eukaryotic repair enzyme that recognizes and removes said non-standard nucleotide from duplex DNA or DNA/RNA duplexes.

11. The method of claim 10, wherein the ligand binds preferentially to an AT-rich or a GC-rich sequence in said second duplex region.

12. The method of claim 10, wherein each DNA molecule comprises a second strand comprising one or more of the same non-standard nucleotide(s) as that present in said first site.

13. The method of claim 10, wherein said modifying agent binds in the minor groove of said DNA molecule.

14. The method of claim 10, wherein said non-standard nucleotide is uracil, and said modifying agent is uracil DNA glycosylase.

15. The method of claim 10, wherein said non-standard nucleotide is a formamidopyrimidine or 8-oxoguanine, and said modifying agent is formamidopyrimidine glycosylase.

16. The method of claim 10, wherein said non-standard nucleotide is thymine glycol, and said modifying agent is $E$ $coli$ endonuclease III.

17. The method of claim 10, wherein said ligand comprises a moiety capable of binding to said first region, and said ligand may also bind to said second region.

18. The method of claim 17, wherein said first duplex region comprises an AT-rich sequence, and said moiety is a distamycin-like moiety that is capable of binding to said AT-rich sequence.

19. The method of claim 1, additionally comprising determining the concentration of said ligand that protects approximately 50 percent of said first sites from modification as an indication of the dissociation constant ($K_d$) of said ligand.

20. The method of claim 19, wherein the amplification of unmodified nucleic acids comprises primer-directed PCR amplification, and approximately 50 percent protection is determined by determining the concentration of ligand that gives a Ct value about 2 higher than the Ct value obtained when the nucleic acid molecule amplified without prior exposure to ligand or modifying enzyme.

21. A method for screening ligands for the ability to bind to nucleotide sequence(s) in nucleic acid molecules, comprising:
(a) providing a set of nucleic acid molecules, each having a first region and a second region, adjacent to said first region, wherein:
(i) in said first region, said nucleic acid molecules comprise a first site that is susceptible to modification by a modifying agent, wherein such modification is effective to block strand-directed duplication by a polymerase enzyme at said first site; and
(ii) said nucleic acid molecules comprise different nucleotide sequences in said second region;
(b) providing a set of different ligands;
(c) contacting said set of nucleic acid molecules with said set of different ligands, under conditions suitable for sequence-dependent binding of one or more ligands to one or more nucleic acid molecules, to form a reaction mixture;
(d) treating the reaction mixture of (c) with said modifying agent, under conditions wherein nucleic acid molecules comprising a ligand bound to said second region are substantially protected from modification at said first site, and nucleic acid molecules wherein a ligand is not bound to said second region are substantially modified at said first site;
(e) after said treatment, removing or inactivating said modifying agent;
(f) after said removal or inactivation, separating ligands that bind to said nucleic acid molecules from unbound ligands, and recovering the ligands that bind to said nucleic acid molecules; and
(g) also after the removal or inactivation of (e), contacting said set of nucleic acid molecules with said polymerase enzyme, under conditions wherein only unmodified nucleic acid strands are amplified;
thereby obtaining a pool of selected ligands that bind in a sequence-dependent manner to one or more nucleotide sequences present in a pool of selected nucleic acid molecules.

22. The method of claim 21 wherein the ligands are heterologous peptides, expressed on the surface of phage particles, each phage particle comprises a nucleic acid molecule encoding the heterologous peptide expressed on its surface, and the pool of selected ligands is a pool of selected phage particles.

23. The method of claim 22, additionally comprising:
(g) amplifying said pool of selected phage particles to produce amplified, selected phage particles;
(h) contacting said pool of selected nucleic acid molecules with said amplified, selected phage particles, under conditions suitable for specific binding of one or more heterologous peptides to one or more nucleic acid molecules, to form a reaction mixture;
(i) treating the reaction mixture of (h) with said modifying agent, under conditions wherein nucleic acid molecules comprising a heterologous peptide bound to said second region are substantially protected from modification, and nucleic acid molecules wherein a heterologous peptide is not bound to said second region are substantially modified at said first site;

(j) after said treatment, removing or inactivating said modifying agent;

(k) after said removal or inactivation, separating amplified, selected phage particles that bind to said selected nucleic acid molecules from unbound amplified, selected phage particles, and recovering the amplified, selected phage particles that bind to said selected nucleic acid molecules;

(l) also after the removal or inactivation of (j), contacting the selected nucleic acid molecules with said polymerase enzyme, under conditions wherein only unmodified nucleic acid molecules are amplified;

thereby obtaining a pool of twice-selected phage particles that bind in a sequence-dependent manner to one or more nucleotide sequences present in a pool of twice-selected nucleic acid molecules.

24. The method of claim 22, wherein said nucleic acid molecules are linked to a substrate, and phage particles that bind to said nucleic acid molecules are separated from unbound phage particles and recovered by washing the substrate to remove unbound phage particles, followed by elution to recover bound phage particles.

25. The method of claim 22, wherein said nucleic acid molecules in the set are double-stranded nucleic acid molecules, said first and second regions are first and second duplex regions, said first site is on a first strand of said nucleic acid molecules, and said amplification comprises amplifying said first strands.

26. The method of claim 25, wherein said nucleic acid molecules are reversibly linked to a substrate, and the method comprises releasing said nucleic acid molecules from said substrate before amplification of said first strands.

27. The method of claim 26, wherein said nucleic acid molecules are reversibly linked to said substrate by a biotin-avidin linkage.

28. The method of claim 25, wherein said first strands of said nucleic acid molecules are not affixed to said substrate, and said method comprises denaturing said double-stranded nucleic acid molecules, thereby releasing said first strands from said substrate, followed by amplification of said first strands.

29. The method of claim 25, wherein said first sites each comprise a non-standard nucleotide that is modified by said modifying agent, wherein such modification is effective to block strand-directed duplication by a polymerase enzyme at said first sites.

30. The method of claim 29, wherein the nucleic acid molecules each comprise a second strand comprising on e or more non-standard nucleotides that can be modified by the modifying agent, and said treating is effective to modify the non-standard nucleotide(s) in the second strand.

31. The method of claim 25, wherein said modifying agent is a restriction enzyme and said first sites comprises a recognition site for said restriction enzyme.

32. The method of claim 31, wherein said nucleic acid molecules comprise a second strand comprising one or more non-standard nucleotides that can be modified by a different modifying agent, said treating additionally comprises treating said nucleic acid molecules with said different modifying agent to modify the non-standard nucleotide(s) in the second strand, and said different modifying agent is removed or inactivated prior to amplification of unmodified nucleic acid strands.

33. The method of claim 25, wherein the amplification of unmodified nucleic acid strands comprises primer-directed PCR amplification.

34. The method of claim 29, wherein the nucleic acid molecules comprise DNA molecules, and the modifying agent is a prokaryotic or eukaryotic repair enzyme that recognizes and removes said non-standard nucleotide from duplex DNA or DNA/RNA duplexes.

35. The method of claim 34, wherein the heterologous peptide binds preferentially to an AT-rich or a GC-rich sequence in said second duplex region.

36. The method of claim 34, wherein each DNA molecule comprises a second strand comprising one or more of the same non-standard nucleotide(s) as that present in said first site.

37. The method of claim 34, wherein said modifying agent binds in the minor groove of said DNA molecule.

38. The method of claim 34, wherein said non-standard nucleotide is uracil, and said modifying agent is uracil DNA glycosylase.

39. The method of claim 34, wherein said non-standard nucleotide is a formamidopyrimidine or 8-oxoguanine, and said modifying agent is formamidopyrimidine glycosylase.

40. The method of claim 34, wherein said non-standard nucleotide is thymine glycol, and said modifying agent is *E coli* endonuclease III.

41. A method for screening a ligand for its ability to bind to one or more nucleotide sequences in a set of double-stranded DNA molecules, comprising:

(a) providing a set of double-stranded DNA molecules, each having a first duplex region and a second duplex region, adjacent to said first duplex region, wherein:

(i) said first duplex region comprises, on a first strand of said DNA molecules, a first site comprising a non-standard nucleotide that is susceptible to modification by a modifying agent, wherein said modifying agent is a prokaryotic or eukaryotic repair enzyme that binds to the minor groove of duplex DNA and removes said non-standard nucleotide from duplex DNA;

(ii) said DNA molecules comprise different nucleotide sequences in said second duplex region; and (iii) said DNA molecules comprise a second strand comprising one or more non-standard nucleotides that can be modified by the modifying agent;

(b) providing a ligand;

(c) contacting said set of DNA molecules with said ligand, under conditions suitable for sequence-dependent binding of said ligand to said nucleic acid molecule, to form a reaction mixture;

(d) treating the reaction mixture of (c) with said modifying agent, under conditions wherein non-standard nucleotides in said DNA molecules are substantially modified, except for non-standard nucleotides at said first site in DNA molecules comprising ligand bound to said second duplex region;

(e) after said treatment, removing or inactivating said modifying agent;

(f) after said removal or inactivation, contacting the DNA molecules with said polymerase enzyme, under conditions wherein only unmodified first strands are amplified by primer-directed PCR amplification, wherein said amplification indicates that the ligand binds to a nucleotide sequence in said second duplex region; and (g) determining the nucleotide sequence of the amplification product in the second duplex region to determine whether the ligand shows binding specificity for one or more nucleotide sequences in said second duplex region.

42. A method for screening peptide ligands for the ability to bind to one or more nucleotide sequences in a set of double-stranded DNA molecules, comprising:
   (a) providing a set of double-stranded DNA molecules linked to a substrate, each having a first duplex region and a second duplex region, adjacent to said first duplex region, wherein:
      (i) said first duplex region comprises, on a first strand of said DNA molecules, a first site comprising a non-standard nucleotide that is susceptible to modification by a modifying agent, wherein said modifying agent is a prokaryotic or eukaryotic repair enzyme that binds to the minor groove of duplex DNA and removes said non-standard nucleotide from duplex DNA;
      (ii) said DNA molecules comprise different nucleotide sequences in said second duplex region; and
      (iii) said DNA molecules comprise a second strand comprising one or more non-standard nucleotides that can be modified by the modifying agent;
   (b) providing a set of different phage particles, wherein each phage particle expresses a heterologous peptide on its surface and comprises a nucleic acid encoding said heterologous peptide;
   (c) contacting said set of DNA molecules with said set of phage particles, under conditions suitable for specific binding of one or more heterologous peptides to one or more DNA molecules, to form a reaction mixture;
   (d) treating the reaction mixture of (c) with said modifying agent, under conditions wherein non-standard nucleotides in said DNA molecules are substantially modified, except for non-standard nucleotides at said first site in DNA molecules comprising heterologous peptide bound to said second duplex region;
   (e) after said treatment, removing or inactivating said modifying agent;
   (f) after said removal or inactivation, washing the substrate to separate phage particles that bind to said DNA molecules from unbound phage particles, and recovering the phage particles that bind to said DNA by elution; and
   (g) also after the removal or inactivation of (e), contacting the DNA molecules with said polymerase enzyme, under conditions wherein only unmodified first strands are amplified by primer-directed PCR amplification;
thereby obtaining a pool of selected phage particles expressing heterologous peptides that bind in a sequence-dependent manner to one or more nucleotide sequences present in a pool of selected DNA molecules.

43. A kit for use in screening one or more ligands for the ability to bind to nucleotide sequence(s) in nucleic acid molecules, comprising:
   (a) a set of nucleic acid molecules, each having a first region and a second region, adjacent to said first region, wherein
      (i) said first region comprises a first site including a non-standard nucleotide that is susceptible to modification by a modifying agent, wherein said modification is effective to block strand-directed duplication by a polymerase enzyme at said first site; and
      (ii) said nucleic acid molecules comprise different nucleotide sequences in said second region; and
   (b) said modifying agent;
   wherein:
   said nucleic acid molecules in the set comprise a double-stranded DNA molecules, said first and second regions are first and second duplex regions, and said first site is on a first strand of said DNA molecules;
   said non-standard nucleotide is a formamidopyrimidine or 8-oxoguanine; and
   the modifying agent is formamidopyrimidine glycosylase.

44. A kit for use in screening one or more ligands for the ability to bind to nucleotide sequence(s) in nucleic acid molecules, comprising:
   (a) a set of nucleic acid molecules, each having a first region and a second region, adjacent to said first region, wherein
      (i) said first region comprises a first site including a non-standard nucleotide that is susceptible to modification by a modifying agent, wherein said modification is effective to block strand-directed duplication by a polymerase enzyme at said first site; and
      (ii) said nucleic acid molecules comprise different nucleotide sequences in said second region; and
   (b) said modifying agent;
   wherein:
   said nucleic acid molecules in the set comprise a double stranded DNA molecules, said first and second regions are first and second duplex regions, and said first site is on a first strand of said DNA molecules;
   said non-standard nucleotide is thymine glycol; and
   said modifying agent is E coli endonuclease III.

45. A kit for use in screening one or more ligands for the ability to bind to nucleotide sequence(s) in nucleic acid molecules, comprising:
   (a) a set of nucleic acid molecules, each having a first region and a second region, adjacent to said first region, wherein
      (i) said first region comprises a first site that is susceptible to modification by a modifying agent, wherein such modification is effective to block strand-directed duplication by a polymerase enzyme at said first site; and
      (ii) said nucleic acid molecules comprise different nucleotide sequences in said second region; and
   (b) said modifying agent;
   wherein said nucleic acid molecules are linked to a substrate.

46. The kit of claim 45, wherein said linkage is a reversible linkage.

47. A kit for use in screening one or more ligands for the ability to bind to nucleotide sequence(s) in nucleic acid molecules, comprising:
   (a) a set of nucleic acid molecules, each having a first region and a second region, adjacent to said first region, wherein
      (i) said first region comprises a first site that is susceptible to modification by a modifying agent, wherein such modification is effective to block strand-directed duplication by a polymerase enzyme at said first site; and
      (ii) said nucleic acid molecules comprise different nucleotide sequences in said second region; and
   (b) said modifying agent; and
   (c) a phage display library.

* * * * *

SEQUENCE LISTING

```
<160> NUMBER OF SEQ ID NOS: 8

<210> SEQ ID NO 1
<211> LENGTH: 80
<212> TYPE: DNA
<213> ORGANISM: Artificial Sequence
<220> FEATURE:
<221> NAME/KEY: misc_feature
<222> LOCATION: (52)..(60)
<223> OTHER INFORMATION: n = any nucleotide
<221> NAME/KEY: misc_feature
<222> LOCATION: ()..()
<223> OTHER INFORMATION: artificial = test binding site

<400> SEQUENCE: 1
tcttggcagc aggauugtcc uuggatccac tacgcagcgc ctccctccac tnnnnnnnnn    60
aaaagggctg gagacgtggc                                                80

<210> SEQ ID NO 2
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: artificial = primer

<400> SEQUENCE: 2
gccacgtctc cagcccttuu                                                20

<210> SEQ ID NO 3
<211> LENGTH: 22
<212> TYPE: DNA
<213> ORGANISM: Artificial Sequence
<220> FEATURE:
<221> NAME/KEY: misc_feature
<222> LOCATION: ()..()
<223> OTHER INFORMATION: artificial = primer

<400> SEQUENCE: 3
tcttggcagc aggauugtcc uu                                             22

<210> SEQ ID NO 4
<211> LENGTH: 23
<212> TYPE: DNA
<213> ORGANISM: Artificial Sequence
<220> FEATURE:
<221> NAME/KEY: misc_feature
<222> LOCATION: ()..()
<223> OTHER INFORMATION: artificial = probe

<400> SEQUENCE: 4
actacgcagc gcctccctcc act                                            23

<210> SEQ ID NO 5
<211> LENGTH: 13
<212> TYPE: DNA
<213> ORGANISM: Artificial Sequence
<220> FEATURE:
<221> NAME/KEY: misc_feature
<222> LOCATION: (1)..(9)
<223> OTHER INFORMATION: n = any nucleotide
<221> NAME/KEY: misc_feature
<222> LOCATION: ()..()
<223> OTHER INFORMATION: artificial = test binding site

<400> SEQUENCE: 5
```

```
nnnnnnnnna aaa                                                          13

<210> SEQ ID NO 6
<211> LENGTH: 13
<212> TYPE: DNA
<213> ORGANISM: Artificial Sequence
<220> FEATURE:
<221> NAME/KEY: misc_feature
<222> LOCATION: (1)..(9)
<223> OTHER INFORMATION: n = any nucleotide
<221> NAME/KEY: misc_feature
<222> LOCATION: ()..()
<223> OTHER INFORMATION: artificial = test binding site

<400> SEQUENCE: 6
nnnnnnnnnu utt                                                          13

<210> SEQ ID NO 7
<211> LENGTH: 12
<212> TYPE: DNA
<213> ORGANISM: Artificial Sequence
<220> FEATURE:
<221> NAME/KEY: misc_feature
<222> LOCATION: (1)..(8)
<223> OTHER INFORMATION: n = any nucleotide
<221> NAME/KEY: misc_feature
<222> LOCATION: ()..()
<223> OTHER INFORMATION: artificial = test binding site

<400> SEQUENCE: 7
nnnnnnnnaa aa                                                           12

<210> SEQ ID NO 8
<211> LENGTH: 12
<212> TYPE: DNA
<213> ORGANISM: Artificial Sequence
<220> FEATURE:
<221> NAME/KEY: misc_feature
<222> LOCATION: (1)..(8)
<223> OTHER INFORMATION: n = any nucleotide
<221> NAME/KEY: misc_feature
<222> LOCATION: ()..()
<223> OTHER INFORMATION: artificial = test binding site

<400> SEQUENCE: 8
nnnnnnnnuu uu                                                           12
```